(12) United States Patent
Huang et al.

(10) Patent No.: US 11,028,073 B2
(45) Date of Patent: Jun. 8, 2021

(54) BUTYLPHTHALIDE-TELMISARTAN HYBRIDS, PREPARATION METHOD AND APPLICATION THEREOF

(71) Applicant: GUANGDONG LONGFU MEDICINE CO., LTD., Zhongshan (CN)

(72) Inventors: Zhangjian Huang, Nanjing (CN); Tao Pang, Nanjing (CN); Cunfang Wang, Zhongshan (CN); Wenbin Zeng, Zhongshan (CN); Jinxiang Deng, Zhongshan (CN); Weijie Wu, Zhongshan (CN); Tingyu Huang, Zhongshan (CN)

(73) Assignee: GUANGDONG LONGFU MEDICINE CO., LTD., Zhongshan (CN)

( * ) Notice: Subject to any disclaimer, the term of this patent is extended or adjusted under 35 U.S.C. 154(b) by 0 days.

(21) Appl. No.: 16/478,400

(22) PCT Filed: Jan. 4, 2018

(86) PCT No.: PCT/CN2018/071308
§ 371 (c)(1),
(2) Date: Jul. 16, 2019

(87) PCT Pub. No.: WO2018/133670
PCT Pub. Date: Jul. 26, 2018

(65) Prior Publication Data
US 2019/0375729 A1     Dec. 12, 2019

(30) Foreign Application Priority Data
Jan. 18, 2017 (CN) .......................... 201710033418.6

(51) Int. Cl.
| | | |
|---|---|---|
| *C07D 235/18* | (2006.01) | |
| *C07D 257/04* | (2006.01) | |
| *C07D 403/10* | (2006.01) | |
| *C07D 403/04* | (2006.01) | |
| *A61P 9/10* | (2006.01) | |
| *A61P 25/16* | (2006.01) | |
| *A61P 29/00* | (2006.01) | |

(52) U.S. Cl.
CPC .............. *C07D 403/04* (2013.01); *A61P 9/10* (2018.01); *A61P 25/16* (2018.01); *A61P 29/00* (2018.01); *C07D 235/18* (2013.01); *C07D 257/04* (2013.01); *C07D 403/10* (2013.01)

(58) Field of Classification Search
CPC ... C07D 235/18; C07D 257/04; C07D 403/10
See application file for complete search history.

(56) References Cited

U.S. PATENT DOCUMENTS

| | | |
|---|---|---|
| 9,388,134 B2 | 7/2016 | Feng et al. |
| 2006/0276523 A1 | 12/2006 | Almirante et al. |
| 2010/0143465 A1 | 6/2010 | Thomas et al. |
| | (Continued) | |

FOREIGN PATENT DOCUMENTS

| | | |
|---|---|---|
| CN | 101134745 A | 3/2008 |
| CN | 101337891 A | 1/2009 |
| | (Continued) | |

OTHER PUBLICATIONS

Chemical Abstracts Registry No. 2102347-46-4, indexed in the Registry file on STN CAS Online Jul. 18, 2017. (Year: 2017).*
Chemical Abstracts Registry No. 2102347-47-5, indexed in the Registry file on STN CAS Online Jul. 18, 2017. (Year: 2017).*
Thompson et al., Current Medicinal Chemistry, Oct. 2002, 9(19), pp. 1751-1762. (Year: 2002).*

(Continued)

*Primary Examiner* — Laura L Stockton
(74) *Attorney, Agent, or Firm* — Kagan Binder, PLLC

(57) ABSTRACT

The invention discloses a butylphthalide-telmisartan heterocomplex, a preparation method and an application thereof. The invention specifically relates to an optically active ring-opening butylphthalide-telmisartan heterocomplex shown in formula I or a pharmaceutically acceptable salt or ester thereof, a preparation method thereof, a pharmaceutical composition containing the compounds, and a pharmaceutical application thereof, particularly application in prevention and treatment of neuroinflammation-related diseases, including ischemic stroke, Alzheimer's disease, brain trauma, Parkinson's disease, multiple sclerosis, depression and so on.

Formula I

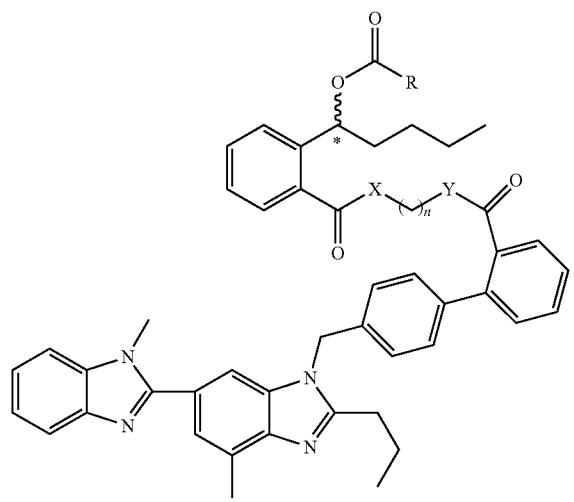

9 Claims, 4 Drawing Sheets

(56) References Cited

U.S. PATENT DOCUMENTS

| | | | |
|---|---|---|---|
| 2015/0057322 A1 | 2/2015 | Feng et al. | |
| 2018/0028451 A1 | 2/2018 | Behrend et al. | |

FOREIGN PATENT DOCUMENTS

| | | | |
|---|---|---|---|
| CN | 103193789 A | 7/2013 | |
| CN | 104628649 A | 5/2015 | |
| CN | 105412077 A | 3/2016 | |
| CN | 105412078 A | 3/2016 | |
| CN | 106800537 A | 6/2017 | |
| JP | 2010530844 A | 9/2010 | |
| JP | 2015098485 A | 5/2015 | |
| JP | 2016160257 A | 9/2016 | |
| WO | 2005011646 A2 | 2/2005 | |
| WO | 2016135175 A1 | 9/2016 | |
| WO | 2018133670 A1 | 7/2018 | |

OTHER PUBLICATIONS

Guttman et al. {Canadian Medical Association Journal, Feb. 4, 2003, 168(3), pp. 293-301. (Year: 2003).*
Thomas et al. {Human Molecular Genetics, 2007, vol. 16, Review Issue 2, pp. R183-R194. (Year: 2007).*
Extended European Search Report for European Counterpart Application No. 18741580.7, dated Oct. 16, 2019 (6 pages).
Japanese Office Action for Japanese Counterpart Application No. 2019-551260, dated Dec. 5, 2019 (2 pages).
Canadian Office Action for Canadian Counterpart Application No. 3,049,604, dated Jul. 29, 2019 (4 pages).
International Search Report, and English Translation thereof, for International Application No. PCT/CN2018/071308, dated Apr. 3, 2018 (8 pages).
First Search Report for Chinese Application No. 201710033418.6, dated Jun. 19, 2019 (1 page).
First Chinese Office Action, and English Translation thereof, for Chinese Application No. 201710033418.6, dated Jun. 6, 2018 (9 pages).
Wang et al., "Advances in Research on 3-n-Butylphthalide Derivatives as Natural Anti-ischemic Stroke Drug", Progress in Pharmaceutical Sciences, 40(2), p. 89-95, Feb. 25, 2016, (7 pages).
Wang et al., "Design, synthesis and biological evaluation of hydrogen sulfide releasing derivatives of 3-n-butylphthalide as potential antiplatelet and antithrombotic agents", The Royal Society of Chemistry, Org. Biomol. Chem., 12, p. 5995-6004, 2014 (10 pages).
Yin et al., "Discovery of a ring-opened derivative of 3-n-butylphthalide bearing NO/H2S-donating moieties as a potential anti-ischemic stroke agent", European Journal of Medicinal Chemistry,115, p. 369-380, Mar. 19, 2016 (12 pages).
Decision to Grant a Patent, and English Translation thereof, for Japanese Application No. 2019-551260, dated Mar. 2, 2020, (5 pages).
Indian Office Action for Indian Application No. 201947028836, dated Jun. 3, 2020, (7 pages).
Canadian Office Action for Canadian Application No. 3,049,604, dated Mar. 3, 2020, (4 pages).
Burnier, "Telmisartan: a Different Angiotensin II Receptor Blocker Protecting a Different Population?", The Journal of International Medical Research, vol. 37, pp. 1662-1679, 2009, (18 pages).
Indian Office Action for Indian Counterpart Application No. 201947028836, dated Feb. 24, 2021 (2 pages).
Kono et al., "Neurovascular Protection by Telmisartan via Reducing Neuroinflammation in Stroke-Resistant Spontaneously Hypertensive Rat Brain after Ischemic Stroke," Journal of Stroke and Cerebrovascular Diseases, vol. 24, Issue 3, pp. 537-547, 2015, DOI: 10.1016/j.jstrokecerebrovasdis.2014.09.037, (11 pages).

* cited by examiner

US 11,028,073 B2

BUTYLPHTHALIDE-TELMISARTAN HYBRIDS, PREPARATION METHOD AND APPLICATION THEREOF

CROSS REFERENCE TO RELATED APPLICATIONS

The present application is a national stage for International Application No. PCT/CN2018/071308, filed on Jan. 4, 2018, which claims priority to Chinese Application No. 201710033418.6, filed on Jan. 18, 2017, both of which are incorporated herein by reference in their entireties.

TECHNICAL FIELD

The present disclosure relates to a butylphthalide-telmisartan hybrid, specifically to an optically active ring-opening butylphthalide-telmisartan hybrid or a pharmaceutically acceptable salt or ester thereof, a preparation method thereof, a pharmaceutical composition containing the compounds, and a medical use thereof, particularly the use in the prevention and treatment of neuroinflammation-related diseases including cerebral ischemic stroke, Alzheimer's disease, brain trauma, Parkinson's disease, multiple sclerosis, depression, and the like, which belongs to the field of pharmaceutical technology.

BACKGROUND

Microglia in the central nervous system (CNS) play a key role in mediating a variety of immune-related diseases, and are categorized into pro-inflammatory type (M1 classical type) and anti-inflammatory type (M2 alternatively activated type). M1 microglia highly express oxidative metabolites (e.g., superoxide and nitric oxide) and pro-inflammatory factors (e.g., TNF-α, IL-10, IL-6 and IL-18) which may produce cytotoxic effect on neurons and glial cells. M2 microglia secrete neurotrophic factors (e.g., Arginase 1, CD206, IL-10 and TGF-01) that may regulate immune responses and promote tissue repair and remodeling.

Telmisartan is a new nonpeptide angiotensin II (Ang II) AT1 receptor antagonist, and may competitively block the binding of Ang II to AT1 so as to antagonize the effects such as vasoconstriction, sympathetic activation and increased secretion of aldosterone caused by Ang II, and therefore may be used to treat high blood pressure. In addition, studies have shown that telmisartan can inhibit the generation of M1 microglia, promote the transformation of microglia into M2, and effectively reduce the occurrence of neuroinflammation, and thus telmisartan has neuroprotective effect. Telmisartan also exerts effects on activating peroxisome proliferator-activated receptor γ (PPARγ), as well as regulating the expression of genes involved in blood glucose, lipogenic metabolism and insulin sensitivity and inhibiting the production of inflammatory factors, and therefore can further be used to improve cardiac remodeling and the treatment of function, and also has a certain effect on the glucose and lipid metabolism disorders and diabetes complications.

Butylphthalide (with trade name of NBP) is the first new drug with independent intellectual property rights in the field of treatment of cerebrovascular diseases in China, and was approved for marketing for the treatment of mild and moderate cerebral ischemic strokes in November 2004. Clinical researches show that butylphthalide can improve the damage of central nervous function and promote the neurological function recovery in patients with acute cerebral ischemic stroke. Pharmacodynamics research in animals suggests that butylphthalide can block multiple pathological processes in brain injury caused by cerebral ischemic stroke, and has strong anti-cerebral ischemia and cerebral protection effects, especially can significantly increase ATP and phosphocreatine levels in the brain of ischemic mouse, significantly reduce the infarction area of local cerebral ischemia in rats, alleviate cerebral edema, improve the cerebral energy metabolism, the microcirculation and blood flow in ischemic cerebral regions, inhibit the apoptosis of neurocyte, and has certain effects on anti-cerebral thrombosis and anti-platelet aggregation (J. Neurol. Sci., 2007, 260, 106). In addition, there are documents demonstrating that butylphthalide can relieve microvascular spasm, inhibit platelet aggregation and the synthesis of thromboxane A2, scavenge free radicals and the like, through affecting the metabolism of arachidonic acid (AA) and selectively inhibiting various pathophysiological processes mediated by AA and metabolites thereof, thus blocking the pathophysiological development processes caused by cerebral ischemia via multiple ways or routes, to protect neurons and repair the function of nerve (J. Cardiovasc. Pharmacol., 2004, 43, 876; ActaPharmacol. Sin., 1998, 19, 117).

Studies shows that potassium 2-(1-hydroxypentyl)-benzoate (PHPB), a ring-opening derivative of butylphthalide, is a water-soluble prodrug of NBP, and can be transformed into NBP rapidly and completely by enzyme or chemical action in vivo and take effects, regardless of oral administration or intravenous injection. The pharmacokinetic characteristics, main metabolites and excretion pathways during the transformation of prodrug PHPB into NBP in vivo after intravenous administration are very similar to those after the direct intravenous administration of NBP (Patent PCT/CN02/00320. 2002). Moreover, the bioavailability of NBP transformed from PHPB in vivo through oral administration of PHPB is nearly doubled compared with that through direct oral administration of NBP, and the disadvantage of poor water solubility of NBP is completely overcome. In addition, pharmacological studies have found that PHPB can significantly improve local cerebral blood flow after ischemia and inhibit excessive platelet aggregation and thrombosis, avoid the damage of mitochondrial function caused by ischemia-reperfusion through various mechanisms, especially protect mitochondria energy metabolism and reduce the activation of the mitochondrial pathway of apoptosis, which is an anti-cerebral ischemic drug with good development prospects (J PharmacolExpTher., 2006, 317, 973).

In the present disclosure, an optically active butylphthalide ring-opening butylphthalide-telmisartan hybrid is designed and synthesized based on the principle of predrug combination.

SUMMARY

The object of the present disclosure is to provide an optically active butylphthalide ring-opening butylphthalide-telmisartan hybrid, a preparation method and a medical use thereof.

In order to solve the above technical problems, the technical solution adopted in the present disclosure is as follows.

There is provided a compound of the present disclosure, which is an optically active butylphthalide-telmisartan hybrid as shown in general formula I, or an optical isomer, an enantiomer, a diastereomer, a racemate or a racemic mixture thereof, or a pharmaceutically acceptable salt thereof:

Formula I

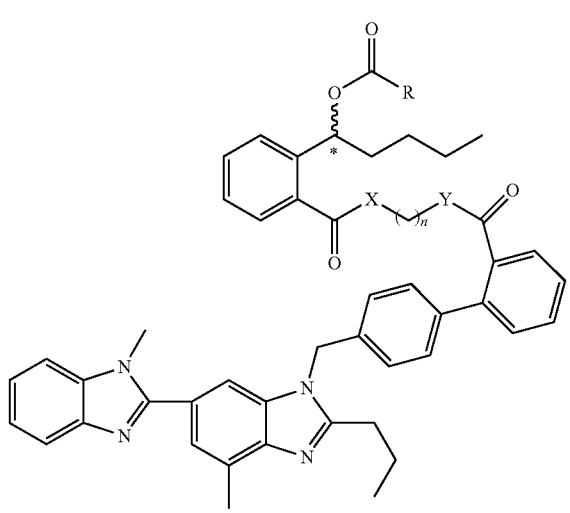

wherein, R represents a hydrogen atom H, linear or branched C1-C10 alkyl, (linear or branched C1-C10 alkylene)-Q, wherein Q represents hydroxyl or halogen;

n represents 1 to 20;

X represents an oxygen atom, a nitrogen atom or a sulfur atom;

Y represents an oxygen atom, a nitrogen atom or a sulfur atom; and the chiral center * is S or R configurated.

Pharmacological experiments demonstrate that the compound of the present disclosure or the optical isomer, the enantiomer, the diastereomer, the racemate or the racemic mixture thereof, or the pharmaceutically acceptable salt thereof has an effect on reducing the increased pro-inflammatory factor TNF-α in primary microglia caused by LPS, inhibiting the increased M1-associated pro-inflammatory factors TNF-α and IL-1β, and promoting M2-associated anti-inflammatory factors CD206 and YM1/2. Moreover, this kind of compounds can significantly reduce cerebral infarction area, improve neurobehavioral function and protect neurons, and therefore may be used to prevent and treat neuroinflammation-related diseases including, but are not limited to, cerebral ischemic stroke, alzheimer's disease, brain trauma, parkinson's disease, multiple sclerosis, depression, and the like.

In a technical solution, there is provided a compound of general formula I or an optical isomer, an enantiomer, a diastereomer, a racemate or a racemic mixture thereof, or a pharmaceutically acceptable salt thereof, wherein R represents a hydrogen atom, dimethylamino, diethylamino, pyrrolyl, piperidinyl, morpholinyl, imidazolyl, an N-methyl piperazinyl or N-hydroxyethylpiperazinyl.

In a technical solution, there is provided a compound of general formula I or an optical isomer, an enantiomer, a diastereomer, a racemate or a racemic mixture thereof, or a pharmaceutically acceptable salt thereof, wherein X represents an oxygen atom or a nitrogen atom.

In a technical solution, there is provided a compound of general formula I or an optical isomer, an enantiomer, a diastereomer, a racemate or a racemic mixture thereof, or a pharmaceutically acceptable salt thereof, wherein Y represents an oxygen atom or a nitrogen atom.

The present disclosure relates to a compound or an optical isomer, an enantiomer, a diastereomer, a racemate or a racemic mixture thereof, or a pharmaceutically acceptable salt thereof, wherein the compound includes, but is not limited to:

2-O-{2-[(1-acetoxyl)n-pentyl]benzoyl}ethylene glycol telmisartan ester (I$_1$)

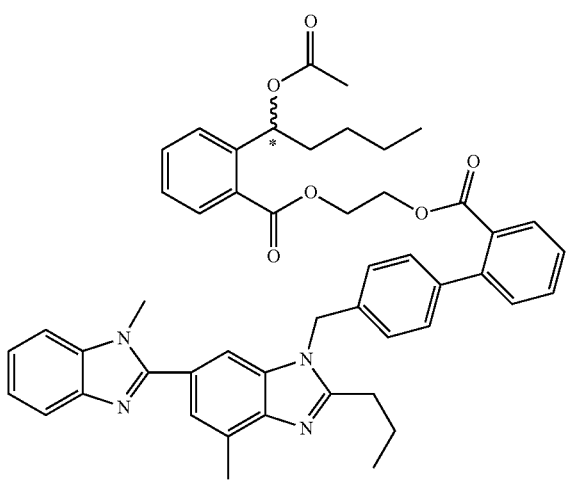

4-O-{2-[(1-acetoxyl)n-pentyl]benzoyl}butanediol telmisartan ester (I$_2$)

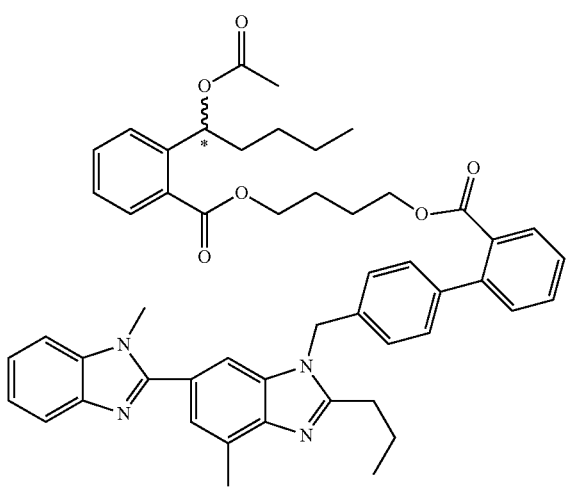

5
8-N-{2-[(1-acetoxyl)n-pentyl]
benzoyl}octanediamine telmisartan amide (I₃)
6
6-O-{2-[(1-acetoxyl)n-pentyl]benzoyl}hexanediol
telmisartan ester (I₅)
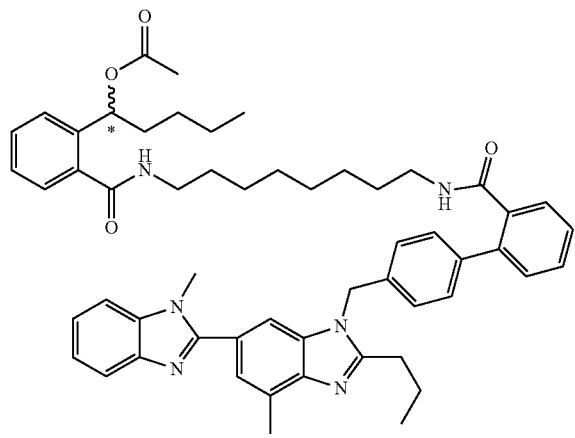
I₃
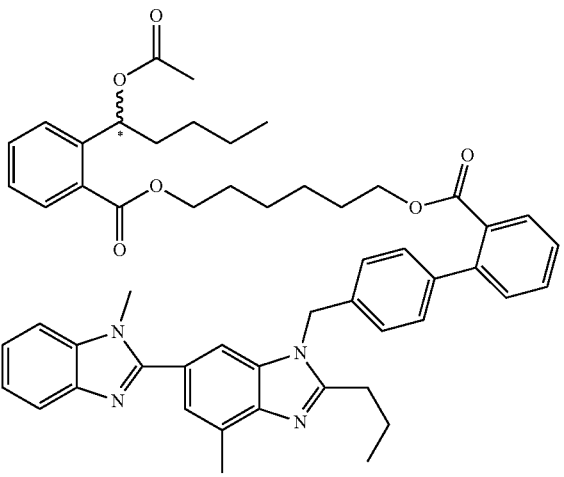
I₅
5-O-{2-[(1-acetoxyl)n-pentyl]benzoyl}pentanediol
telmisartan ester (I₄)
8-O-{2-[(1-acetoxyl)n-pentyl]benzoyl}octanediol
telmisartan ester (I₆)
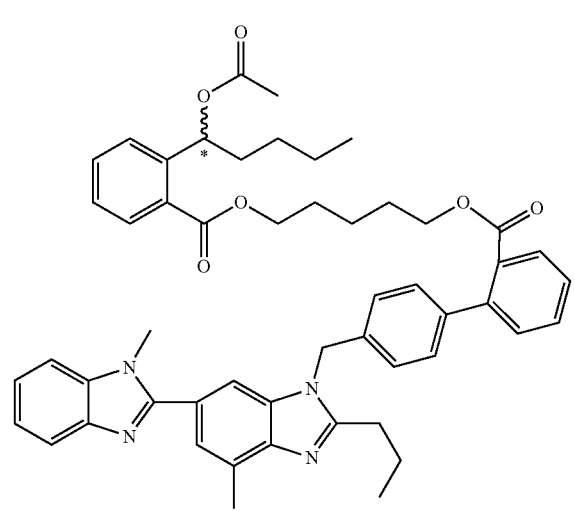
I₄
I₆

7
6-N-{2-[(1-acetoxyl)n-pentyl]
benzoyl}hexanediamine telmisartan amide (I₇)
8
p-methylbenzoyl octanediamine telmisartan amide
(I₉)
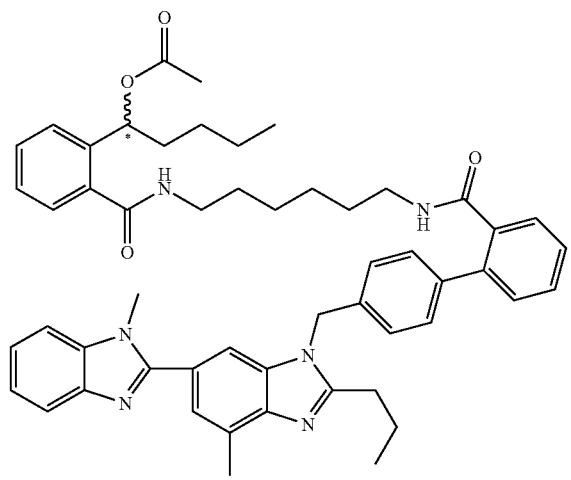
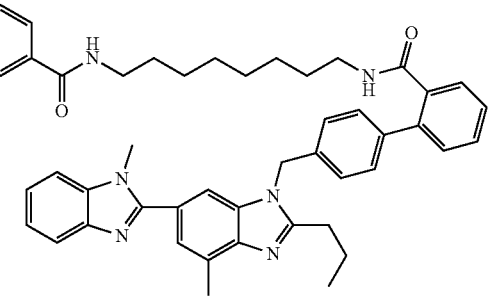
4-N-{2-[(1-acetoxyl)n-pentyl]
benzoyl}butanediamine telmisartan amide (I₈)
3, 5-dichlorobenzoyl octanediamine telmisartan
amide (I₁₀)
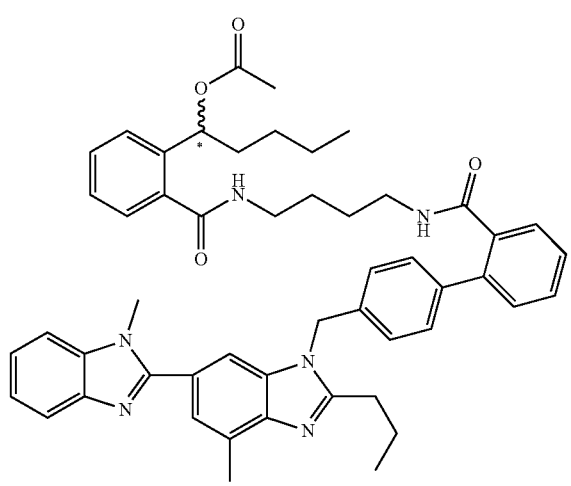
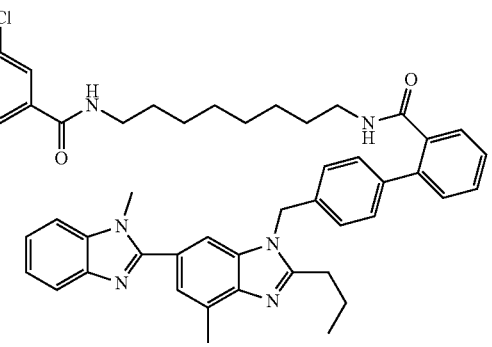

9
4-cyanobenzoyl octanediamine telmisartan amide
(I₁₁)
10
m-methoxybenzoyl octanediamine telmisartan amide (I₁₃)
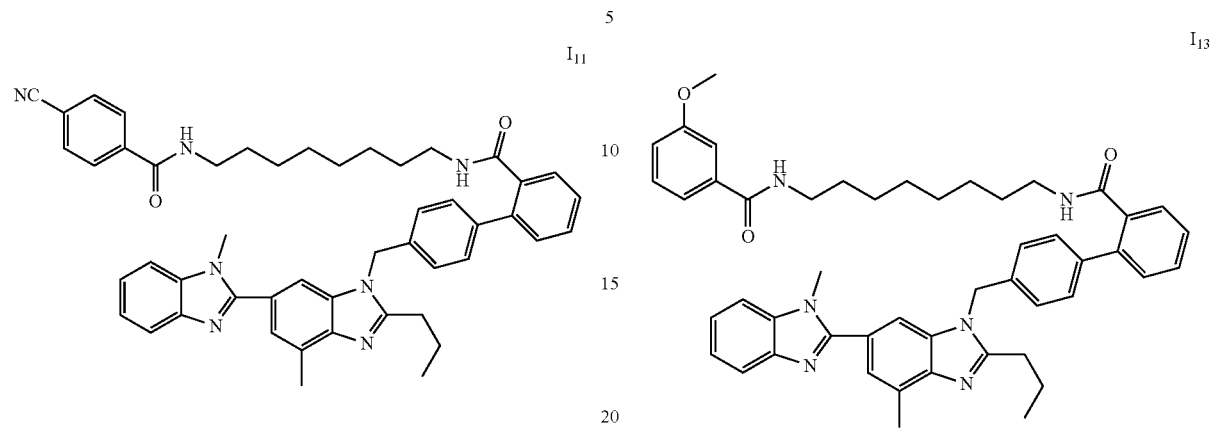
o-hydroxybenzoyl octanediamine telmisartan amide
(I₁₄)
p-nitrobenzoyl octanediamine telmisartan amide
(I₁₂)
8-N-{2-[(1-acetoxyl)n-pentyl]benzoyl}octanediamine candesartan amide (I₁₅)
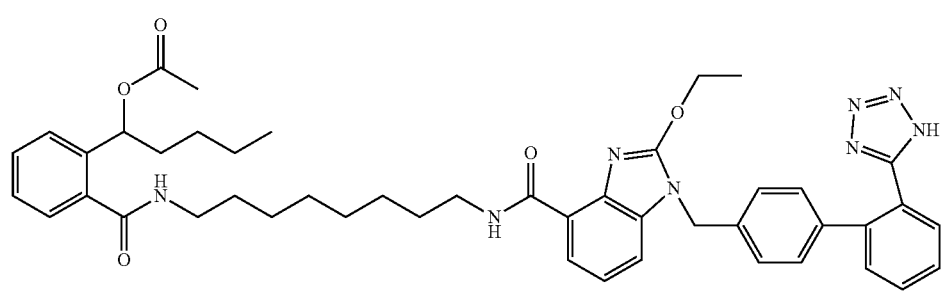

8-N-{2-[(1-acetoxyl)n-pentyl]
benzoyl}octanediamine valsartan amide (I₁₆)

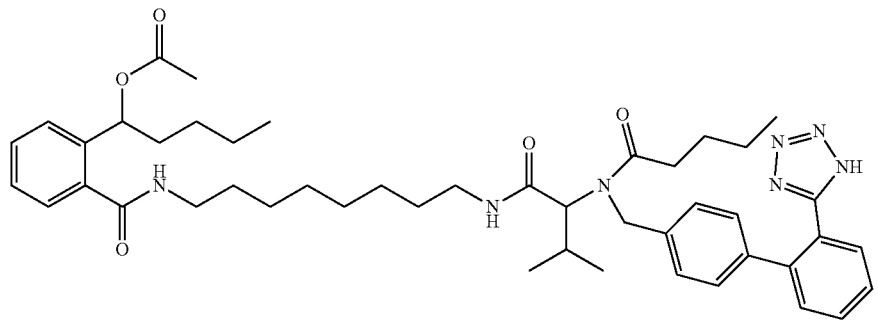

8-N-{2-[(1-acetoxyl)n-pentyl]
benzoyl}octanediamine losartan amide (I₁₇)

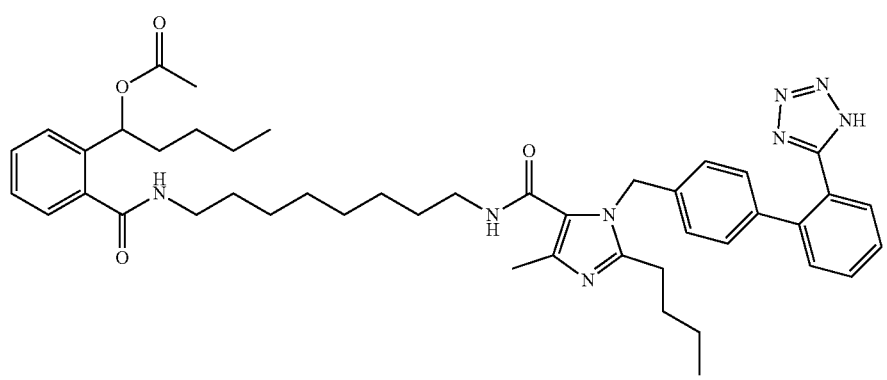

The enantiomers and diastereomers, as well as medicinal acid addition salts of the preferred compounds of the present disclosure constitute the complete part of the disclosure. The medicinal acid includes hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulfonic acid, camphoric acid, oxalic acid, and the like.

Specifically, the medicinal acid addition salt of the compound as shown in general formula I is preferably selected from the group consisting of the following compounds:

8-N-{2-[(1-acetoxyl)n-pentyl]benzoyl}octanediamine telmisartan amide hydrochloride (II)

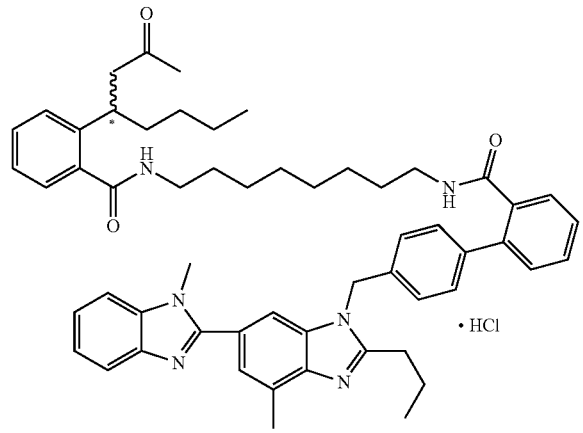

II

The reference number of compound in the following pharmacological experiments is equivalent to the compound corresponding to the reference number herein.

Another object of the present disclosure is to provide a preparation method of the compound of general formula I characterized in that:

(S)- or (R)-butylphthalide is subject to saponification and acidification to give a ring-opening lactone compound III, the compound III is esterified with an acyl chloride compound (RCOCl) to give an ester compound IV, compound IV is condensed with a diol (or a diamine, ect.) having a different carbon chain length to give an intermediate V, and the intermediate V is further condensed with telmisartan to give a target compound I; alternatively, telmisartan is first condensed with a diol (or a diamine, ect.) having a different carbon chain length to give an intermediate VI, and then the intermediate VI is condensed with the ester compound IV to give the target compound I; the synthetic route is as follows:

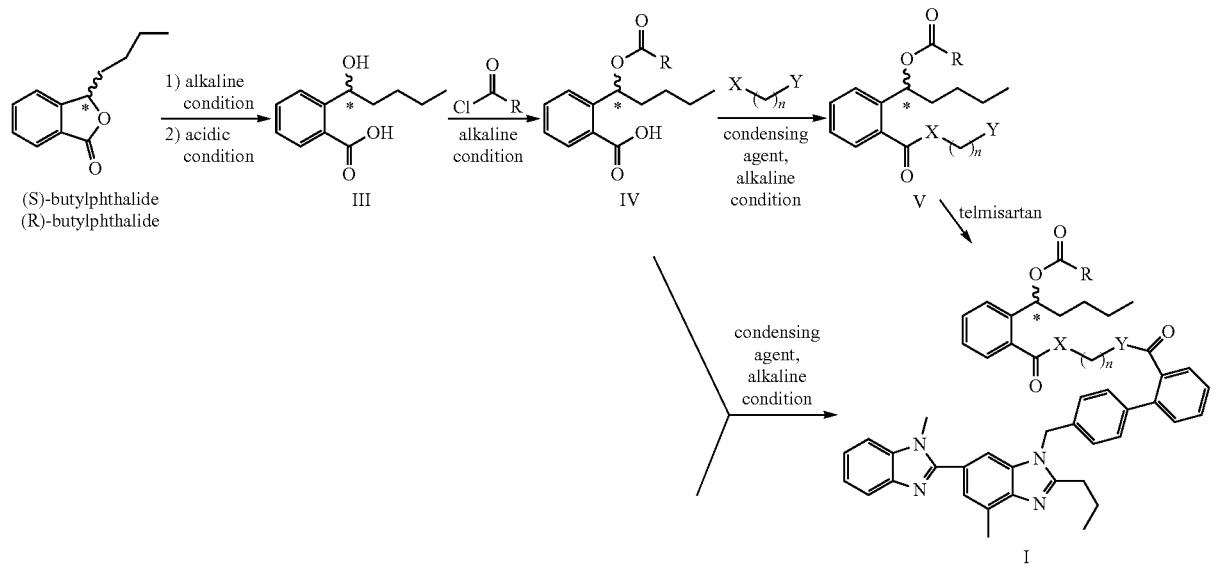

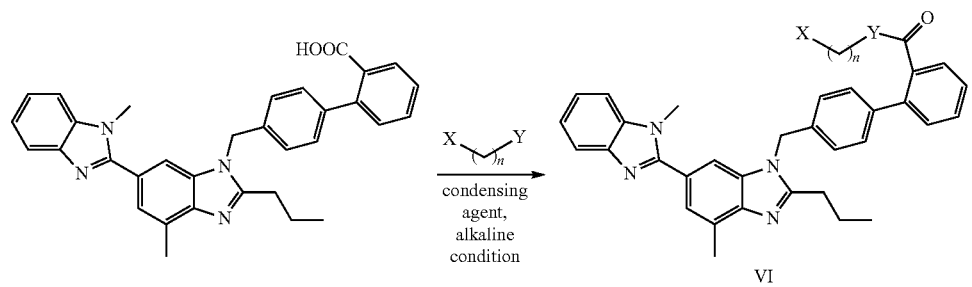

wherein, R is as defined above.

The specific conditions of each reaction step in the preparation method of the compound of general formula I of the present disclosure are as follows.

In the step of preparing the compound IV from the compound III, the solvent is selected from one or more of the group consisting of acetonitrile, dichloromethane, chloroform, ethyl acetate, acetone, tetrahydrofuran, N, N-dimethylformamide, dimethyl sulfoxide and dioxane; the base is selected from the group consisting of potassium carbonate, sodium carbonate, sodium bicarbonate, sodium hydroxide, potassium hydroxide, pyridine, 4-methylaminopyridine, triethylamine, and N, N-diisopropylmethylamine; and the reaction temperature is from −20° C. to reflux temperature.

In the step of preparing the compound V from the compound IV, the solvent is selected from one or more of the group consisting of acetonitrile, dichloromethane, chloroform, ethyl acetate, acetone, tetrahydrofuran, N, N-dimethylformamide, dimethyl sulfoxide and dioxane; the condensing agent is selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide; the base is selected from the group consisting of pyridine, 4-methylaminopyridine, triethylamine, and N, N-diisopropylmethylamine; and the reaction temperature is from −20° C. to reflux temperature. More preferably, the solvent is dichloromethane, the condensing agent is 1-(3-dimethylaminopropyl)-3-ethylcarbodiimide hydrochloride, the base is 4-methylaminopyridine, and the reaction temperature is room temperature.

In the step of preparing the compound I from the compound V, the solvent is selected from one or more of the group consisting of acetonitrile, dichloromethane, chloroform, ethyl acetate, acetone, tetrahydrofuran, N, N-dimethylformamide, dimethyl sulfoxide and dioxane; the condensing agent is selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide; the base is selected from the group consisting of pyridine, 4-methylaminopyridine, triethylamine, and N, N-diisopropylmethylamine; and the reaction temperature is from −20° C. to reflux temperature. More preferably, the solvent is dichloromethane, the condensing agent is 1-(3-dimethylaminopropyl)-3-ethylcarbodiimide hydrochloride, the base is 4-methylaminopyridine, and the reaction temperature is room temperature.

In the step of preparing the compound VI from telmisartan, the solvent is selected from one or more of the group consisting of acetonitrile, dichloromethane, chloroform, ethyl acetate, acetone, tetrahydrofuran, N, N-dimethylformamide, dimethyl sulfoxide and dioxane; the condensing agent is selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide; the base is selected from the group consisting of pyridine, 4-methylaminopyridine, triethylamine, and N, N-diisopropylmethylamine; and the reaction temperature is from −20° C. to reflux temperature. More preferably, the solvent is dichloromethane, the condensing agent is 1-(3-dimethylaminopropyl)-3-ethylcarbodiimide hydrochloride, the base is 4-methylaminopyridine, and the reaction temperature is room temperature.

In the step of preparing the compound I from the compound IV and the compound VI, the solvent is selected from one or more of the group consisting of acetonitrile, dichloromethane, chloroform, ethyl acetate, acetone, tetrahydrofuran, N, N-dimethylformamide, dimethyl sulfoxide and dioxane; the condensing agent is selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide; the base is selected from the group consisting of pyridine, 4-methylaminopyridine, triethylamine, and N, N-diisopropylmethylamine; and the reaction temperature is from −20° C. to reflux temperature. More preferably, the solvent is dichloromethane, the condensing agent is 1-(3-dimethylaminopropyl)-3-ethylcarbodiimide hydrochloride, the base is 4-methylaminopyridine, and the reaction temperature is room temperature.

All the intermediates or target compounds may be purified according to conventional separation techniques, separated into isomers thereof by conventional separation techniques if desired, and converted to medicinal acid or base addition salts as needed.

Another object of the present disclosure is to provide a preparation method of the compound of general formula II comprising:

dissolving compound $I_3$ into a solvent, adding a saturated solution of hydrogen chloride in the solvent and stirring to obtain the compound II; the synthetic route is as follows:

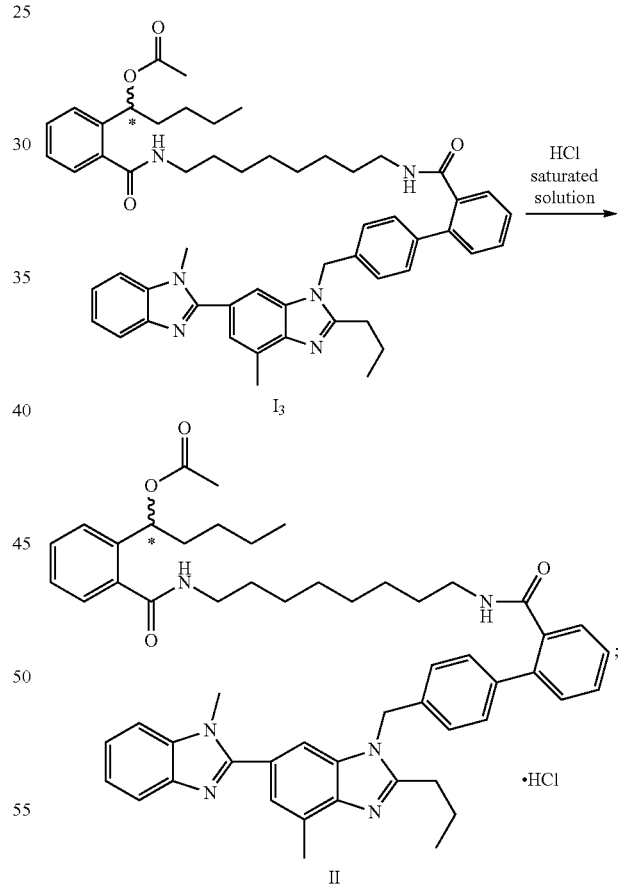

the solvent is selected from one or more of the group consisting of acetonitrile, dichloromethane, chloroform, ethyl acetate, acetone, tetrahydrofuran, N, N-dimethylformamide, dimethyl sulfoxide and dioxane; and the reaction temperature is from −20° C. to reflux temperature.

The preparation of II from I is characterized in that the solvent is ethyl acetate, and the reaction temperature is room temperature.

A further object of the present disclosure is to provide a pharmaceutical composition comprising an effective amount of the compound of general formula I or the optical isomer, the enantiomer, the diastereomer, the racemate or the racemic mixture thereof, or the pharmaceutically acceptable salt thereof and a medicinal carrier.

Still a further object of the present disclosure is to provide a use of the compound of general formula I in the preparation of drugs for preventing or treating neuroinflammation-related diseases, especially for preventing or treating cerebral ischemic stroke, alzheimer's disease, brain trauma, parkinson's disease, multiple sclerosis, depression, and the like.

In the present disclosure, the compound of general formula I and the pharmaceutically acceptable salt thereof, as well as the solvates of these compounds (collectively referred to herein as "therapeutic drug") may be administrated to a mammal alone, or preferably administered in combination with a medicinal carrier or diluent according to standardized pharmaceutical method. The administration may be carried out by various routes, including oral, parenteral or topical administration. The parenteral administration as referred herein includes, but is not limited to, intravenous injection, intramuscular injection, intraperitoneal injection, subcutaneous injection and transdermal administration.

Pharmacological Tests and Results of Representative Compounds of the Present Disclosure are Partially Shown as Follows.

1. In Vitro Model for Screening Anti-Inflammatory Drugs and Model for Screening Nrf2-Activating Drugs 1.1 In Vitro Model for Screening Anti-Inflammatory Drugs:

The primary microglia were extracted from the brain of mouse and cultured, were pre-administrated with 1 μM or 5 μM drugs for 3 h, and then stimulated with 100 ng/mL lipopolysaccharide (LPS) for 5 h. The supernatant of cell culture was extracted, and the expression level of TNF-α in the supernatant was determined by ELISA method. It can be seen from FIG. 1, I3 can significantly inhibit LPS-induced TNF-α release in mouse primary microglia.

1.2 In Vitro Model for Screening Nrf2-Activating Drugs:

BV2 cells were transfected with Neh2-Luciferase reporter gene plasmid for 6 h, replaced a normal serum-containing medium and cultured for 24 h, then incubated with drug for 24 h, and treated with Reporter Lysis Buffer for 20 min. The Reporter Lysis Buffer was added to a 96-well plate, and the activity of luciferase was measured. Positive drug Oltipraz as Nrf2 activator can significantly promote the activation of Nrf2. Compared with the above, 1 μM and 10 μM of I3, 10 μM of I7 and 10 μM of I8 can significantly activate the activity of intracellular Nrf2.

2. Study on Neuroprotective Effect of 13 in Rats with Transient Middle Cerebral Artery Occlusion (tMCAO)

Experimental method: 75 SD male rats weighing 300±20 g were raised under the condition of 25° C. and relative humidity of 60% to 75% for 1 week for experiment. Rats were randomized into 5 groups: sham group, vehicle group, drug administration group at 24 h after ischemia, drug administration group at 6 h after ischemia, drug administration group at 4 h after ischemia, respectively, with 15 animals in each group.

Establishment of transient middle cerebral artery occlusion (tMCAO) rat model: The rats were anesthetized by intraperitoneal injection of chloral hydrate, and lying on an operating table with limbs fixed with string. An incision was made in the middle of the neck and the skin and subcutaneous tissue were incised to expose the digastric muscle, the right common carotid artery (CCA) was isolated and ligated at proximal end, the right external carotid artery (ECA) and internal carotid artery (ICA) were isolated upward, and the superior thyroid artery and occipital artery were isolated, ligated, and cut off. ECA was ligated and cut off, ICA was clamped at the distal end with an arterial clip, and then a small opening was cut at the intersection of ECA and ICA near the ECA. A nylon thread with paraffin coated on one end was inserted from the small cut opening into the internal carotid artery at the intersection of the internal and external carotid arteries and further into the anterior cerebral artery at the proximal end, to block the blood supply to the middle cerebral artery on this side. At 120 minutes after ischemia, the nylon thread was withdrawn at the incision of the external carotid artery to achieve the reperfusion of the middle cerebral artery. The room temperature during surgery was controlled at 25 to 27° C.

Administration method: administrating after surgery with a concentration of 1 mg/kg. Drug administration group at 4 h after ischemia was administrated at 4 h after ischemia, and once again after 24 h. Drug administration group at 6 h after ischemia was administrated at 6 h after ischemia, and once again after 24 h. Drug administration group at 24 h after ischemia was administrated once at 24 h after ischemia.

After the time window for administration of 13 was determined, administration at 4 hour post-ischemia was selected as the subsequent testing time point. 95 SD male rats were randomized into 7 groups: sham group, vehicle group, NBP group, Telm group, NBP+Telm group, 13 group and edaravone group, respectively. The surgical procedure was as described above, NBP (1 mg/kg), Telm (1 mg/kg), NBP (1 mg/kg)+Telm (1 mg/kg), 13 (1 mg/kg) and edaravone (3 mg/kg) were administrated at 4 hour post-ischemia, and once again at 24 h, respectively. The infarct volume and neurobehavioral score were determined at 48 h post-ischemia.

2.1 Determination of the Infarct Volume (TTC Staining):

At 48 h post-ischemia, the rats were anesthetized with pentobarbital sodium, decapitated to get brain quickly, olfactory bulb, cerebellum and lower brain stem were removed, and coronal was cut into 6 slices. Then the brain slices were placed in the solution containing 4% TTC and 1 mol/L of $K_2HPO_4$, incubated at 37° C. for 30 min in the dark, during which the brain slices were flipped every 7 to 8 min. After TTC staining, the normal cerebral tissue showed rosy and the infarcted tissue was white. Images were taken after staining, and the infarct volume was calculated using an image analysis software. The percentage of infarct volume is calculated by the following formula: infarct area/total brain cross-sectional area×100%.

2.2 Neurobehavioral Function Score:

The neurobehavioral function score of tMCAO rats were scored at 48 h after ischemia. Criteria for scoring is as follows: 0 point, no symptoms of nerve damage; 1 point, inability of fully extending forepaw at the healthy side; 2 points, circling to the healthy side; 3 points, tilting toward the healthy side; 4 points, inability of spontaneous walking and losing consciousness.

Experimental Results:

2.1 Test Results of the Infarct Volume in tMCAO Rats:

As shown in FIG. 2, compared with vehicle group, 13 administrating at each time point significantly reduced the infarct volume, wherein the administration group at 4 h post-ischemia has the strongest effect. Meanwhile, compared with NBP group, Telm group and NBP+Telm group, I3 had a more pronounced effect on reducing the infarct volume, and had the same effect as the edaravone group, as shown in Table 1.

TABLE 1

Effects of I3, constituent compounds thereof and Edaravone on reducing infarct volume in rats with tMCAO

| Groups | Infarction rate (%) | SD |
|---|---|---|
| sham group | 0 | 0 |
| vehicle group | 33.04768 | 4.460327 |
| tMCAO + I3 group (administrated after 24 h) | 20.71811 | 9.277905 |
| tMCAO + I3 group (administrated after 6 h) | 13.07053 | 7.106176 |
| tMCAO + I3 group (administrated after 4 h) | 6.654898 | 3.738677 |
| tMCAO + NBP group | 20.99379 | 8.051519 |
| tMCAO + Telm group | 11.57468 | 4.538631 |
| tMCAO + Telm + NBP group | 12.46524 | 8.356078 |
| tMCAO + Edaravone group | 6.183 | 3.805 |

2.2 Measurement Results of Neurological Function Score:

As shown in FIG. 2, compared with the vehicle group, administration of I3 at each time point significantly reduced ischemia-induced neurological function score of I/R rats, i.e., can significantly improve the neurological function of animals. Meanwhile, compared with NBP, Telm and NBP+Telm, I3 had a more pronounced effect on improving the neurological function and had the same effect as the edaravone group, as shown in Table 2.

TABLE 2

Effects of I3, constituent compounds thereof and Edaravone on improving the neurobehavioral function

| Groups | Neurobehavioral score | SD |
|---|---|---|
| Sham group | 0 | 0 |
| vehicle group | 2.8 | 0.421637 |
| tMCAO + I3 group (administrated after 24 h) | 1.181818 | 0.6030227 |
| tMCAO + I3 group (administrated after 6 h) | 1.866667 | 0.3518658 |
| tMCAO + I3 group (administrated after 4 h) | 2.384615 | 0.6504436 |
| tMCAO + NBP group | 2.7 | 0.4830459 |
| tMCAO + Telm group | 1 | 0.7559289 |
| tMCAO + Telm + NBP group | 0.9 | 0.5676462 |
| tMCAO + I3 group | 1.181818 | 0.6030227 |
| tMCAO + Edaravone group | 1.555556 | 0.7264832 |

3. Study on the Protective Effect of I3 on Permanent Middle Cerebral Artery Occlusion (pMCAO)

Experimental method: Surgical method was described as the operation method for the above tMCAO. The thread embolism remained in the brain of rats without pulling out, and rotarod performance was tested every day. Brains were taken out at 72 h after ischemia for the determination of infarct volume and neurobehavioral score. The process of the rotarod performance test was as follows: rats were placed on a rotating rod of which the speed was accelerated from 4 rpm up to the maximum speed of 40 rpm within 5 minutes. Rats were trained for 3 to 7 days before model establishment, the rotarod performance was tested at 1, 2 and 3 days after pMCAO, respectively, and the falling time of rats were recorded.

The results showed that I3 significantly reduced the infarct volume and improved neurobehavioral impairment, and has better effects on improving the neurobehavioral than Edaravone, as shown in Tables 3, 4 and 5.

TABLE 3

Effects of I3 and Edaravone on reducing the infarct volume in rats caused by permanent middle cerebral artery occlusion

| Groups | Infarction rate (%) | SD |
|---|---|---|
| Sham group | 0 | 0 |
| Vehicle group | 30.82191 | 5.78276 |
| pMCAO + I3 group | 12.47746 | 4.24391 |
| pMCAO + Edaravone group | 16.69789 | 5.41495 |

TABLE 4

Effects of I3 and Edaravone on improving the neurobehavioral function in rats with permanent middle cerebral artery occlusion

| Groups | Neurobehavioral score | SD |
|---|---|---|
| Sham group | 0 | 0 |
| Cerebral ischemia group | 2.666667 | 0.5 |
| Cerebral ischemia + I3 group | 1.6 | 0.6992059 |
| Cerebral ischemia + Edaravone group | 1.7 | 0.6749486 |

TABLE 5

Results of the rotarad performance of I3 and Edaravone

| Groups | Before modeling | | Day 1 | | Day 2 | | Day 3 | |
|---|---|---|---|---|---|---|---|---|
| | Falling time | SD | Falling time | SD | Falling time | SD | Falling time | SD |
| Sham group | 273.00 | 23.43 | 300.00 | 0.00 | 300.00 | 0.00 | 296.67 | 3.06 |
| Cerebral ischemia group | 287.30 | 19.84 | 34.20 | 26.88 | 43.11 | 26.50 | 57.80 | 19.01 |
| Cerebral ischemia + I3 group | 279.10 | 32.14 | 68.63 | 44.65 | 94.00 | 50.32 | 125.13 | 54.57 |
| Cerebral ischemia + Edaravone group | 292.17 | 11.43 | 56.33 | 31.65 | 64.00 | 30.00 | 74.00 | 27.83 |

4. Effect of AMPK Pathway on the Neuroprotective Effect of I3

The experimental method was manipulated as described in 2. At 30 min before the administration of I3, rats were intraperitoneally injected with 20 mg/kg of AMPK inhibitor Compound C, and the volume of the ipsilateral hemisphere infarct and the neurobehavioral score were determined at 48 h post-ischemia. Western blot analysis was performed on ischemic brain tissue to determine the content of phosphorylated AMPK (p-AMPK) in the cerebral cortex at the infarct side. The results showed that pre-administration of Compound C significantly attenuate the neuroprotective effect of I3 on transient ischemic attack, and inhibit the increase of AMPK activity induced by I3.

TABLE 6

Pre-administration of Compound C (CC) inhibits the effect of I3 on reducing the infarction area in rats with tMCAO.

| Groups | Infarction rate (%) | SD |
|---|---|---|
| Sham group | 0 | 0 |
| Vehicle group | 33.04768 | 4.460327 |
| tMCAO + I3 group | 6.654898 | 3.738676 |
| tMCAO + I3 + CC group | 15.40428 | 2.989042 |

TABLE 7

Pre-administration of Compound C (CC) inhibits the effect of I3 on the neurobehavioral function recovery in rats with tMCAO.

| Groups | Neurobehavioral score | SD |
|---|---|---|
| Sham group | 0 | 0 |
| Vehicle group | 2.8 | 0.42164 |
| tMCAO + I3 group | 1.181818 | 0.60302 |
| tMCAO + I3 + CC group | 2.625 | 0.51755 |

Advantageous Effects in the present disclosure, the butylphthalide-telmisartan hybrid is designed and synthesized, and in vitro activity study indicates that the butylphthalide-telmisartan hybrid exerts double agonistic activity towards both of Nrf2 and AMPK activation. In a number of in vivo models, the hybrid exerts stronger anti-cerebral ischemia activity than a combination of butylphthalide with telmisartan, and also shows stronger anti-cerebral ischemia activity than Edaravone. The pharmaceutical composition containing these compounds and the medical use thereof have a good application prospect particularly in the prevention and treatment of neuroinflammation-related diseases, including cerebral ischemic stroke, Alzheimer's disease, brain trauma, Parkinson's disease, multiple sclerosis, depression, ect.

BRIEF DESCRIPTION OF THE DRAWINGS

In FIGS. 1A and 1B, mouse primary microglia are pre-incubated with 1 μM or 5 μM of test compounds for 3 hours, then stimulated with LPS for 5 hours, and the protein content of pro-inflammatory factor TNF-α is determined by ELISA method. In FIG. 1C, the activations of the compounds on Nrf2 are tested by Luciferase Reporter Assay.

In FIG. 2, tMCAO models are established in male rats of 260 to 280 g (thread embolism is pulled out from the rats after 2 hour ischemia, resulting in reperfusion), 13 compound (1 mg/kg) is intravenously injected at 4 h post-ischemia, and intravenously injected again at 24 h post-ischemia. At 48 h post-ischemia, the brain tissue is cut into 6 uniform slices and stained using 2,3,5-triphenyltetrazolium chloride (TTC) to determine the infarction area (the white region represents ischemic region and the red region represents non-ischemic region), and the neurobehavioral feature is determined by Longa test, wherein the total score is 4 points, 0 point: no abnormal behavior; 1 point: left forepaw could not fully extend, indicating mild neurological function deficit; 2 points: the rat circles to the left during walking, indicating moderate neurological function deficit; 3 points: the rat tilts to the left side during walking or palsies, indicating severe neurological function deficit; 4 points: the rat cannot walk spontaneously, losing consciousness.

In FIG. 3, pMCAO model is established on male rats of 260 to 280 g (thread embolism is not pulled out, resulting in permanent ischemia), the administration method is the same as that in FIG. 2, and the infract volume, neurobehavioral scores and rotarod test were determined at 72 h after ischemia, as described above.

In FIG. 4, 20 mg/kg Compound C (AMPK inhibitor) is intraperitoneally injected at 3.5 h after ischemia, I3 compound (1 mg/kg) is intravenously injected at 4 h after ischemia, and the infarct volume and neurobehavioral scores were determined after 48 hour ischemia.

DETAILED DESCRIPTION OF THE EMBODIMENTS

Figure 1:
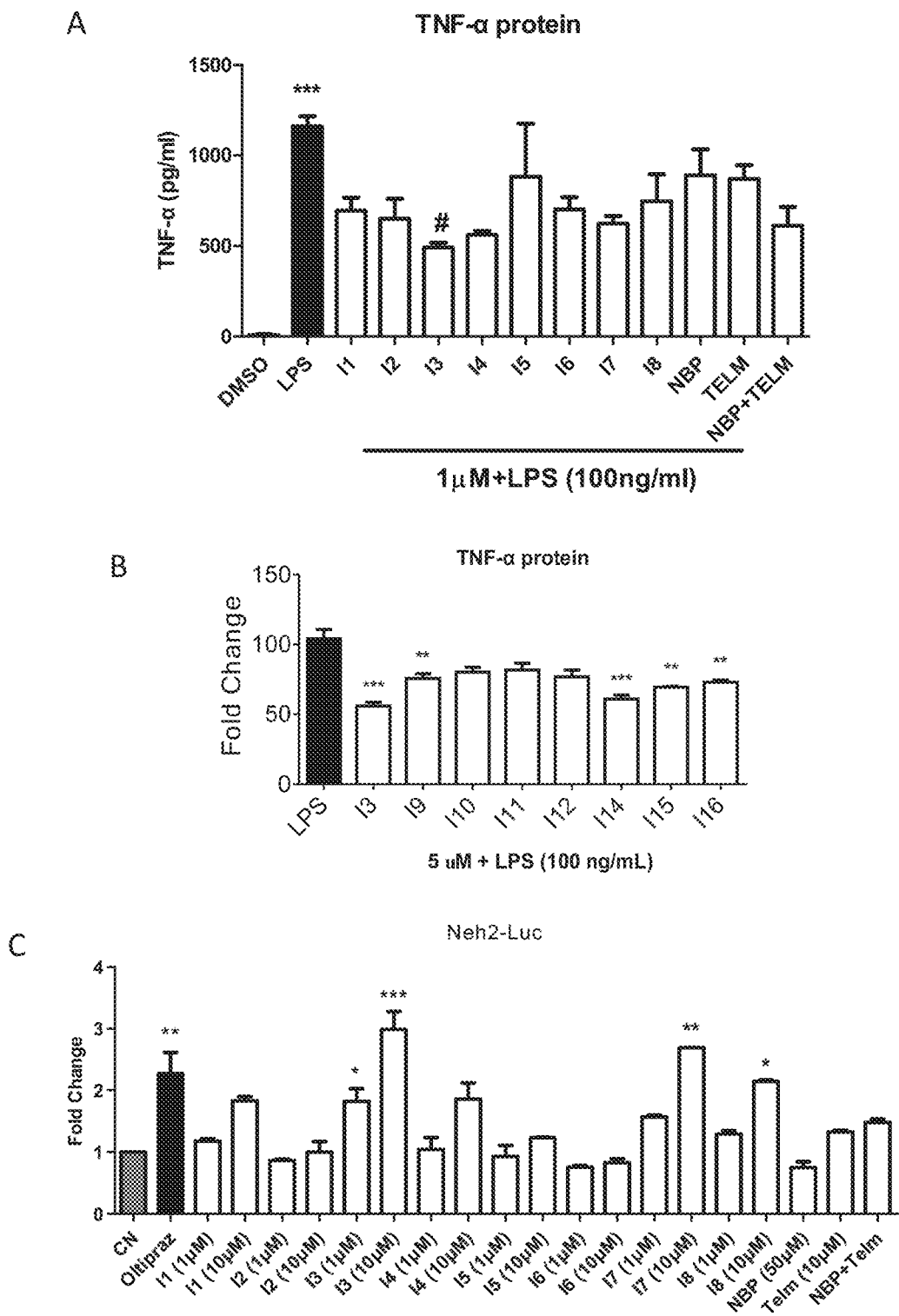
FIG. 1 shows a result of experiments of screening the compounds of the present disclosure on inhibiting the inflammatory factor TNF-α induced by lipopolysaccharide (LPS) and on activating Nrf2 in vitro.
Figure 2:
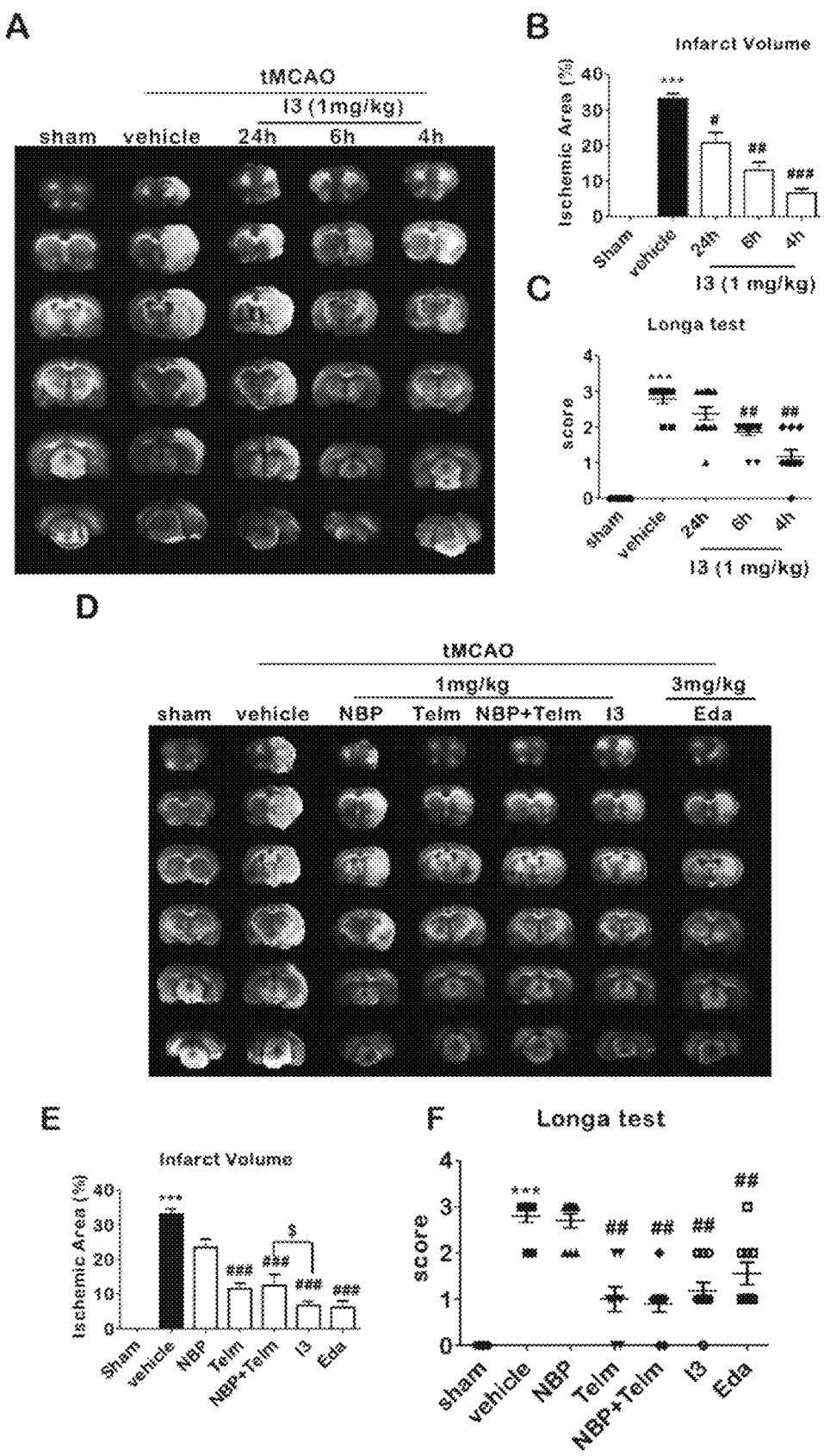
FIG. 2 shows a neuroprotective effect of the representative compound 13 of the present disclosure on transient middle cerebral artery occlusion (tMCAO) rats.
Figure 3:
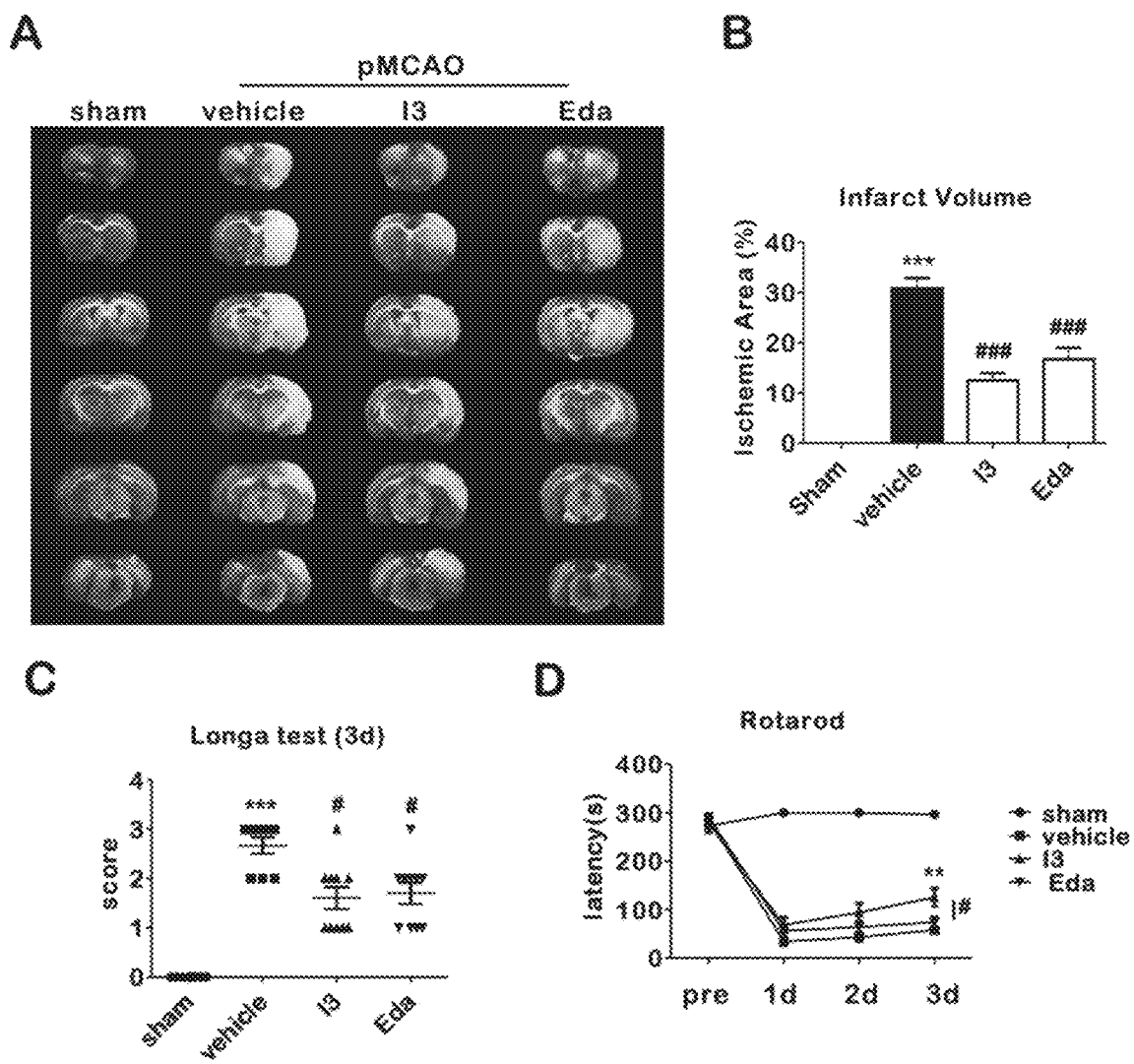
FIG. 3 shows a neuroprotective effect of the representative compound 13 in present disclosure on permanent middle cerebral artery occlusion (pMCAO) rat model.
Figure 4:
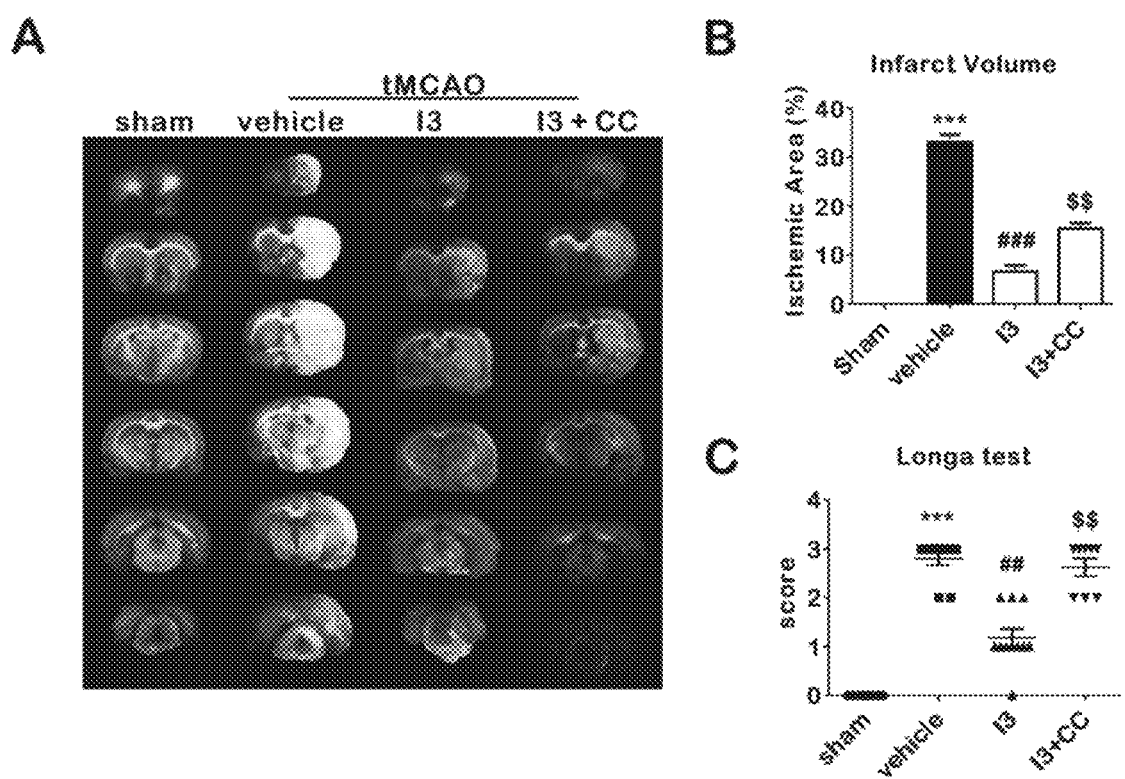
FIG. 4 shows the effect of AMPK pathway on the neuroprotective effect of compound I3.

In order to further illustrate the present disclosure, a series of embodiments are described below, which are completely illustrative and are only used to describe the present disclosure in detail and should not be construed as a limit to the present disclosure.

Example 1

Synthesis of 2-(1-hydroxy-n-pentyl)benzoic acid (III)

1.24 g (6.5 mmol) of NBP was dissolved in 10 mL of methanol, 10 mL of 2M NaOH solution was added. The reaction solution was refluxed with stirring for 0.5 h, evaporated under reduced pressure to remove methanol, diluted by addition of 10 mL of distilled water, cooled to −5° C., acidified to pH 2 to pH 3 with 5% diluted hydrochloric acid under vigorous stirring. The mixture was extracted with diethyl ether (15 mL×3), and directly transferred to the next reaction without any purification.

Example 2

Synthesis of 2-(1-acetyl-n-pentyl)benzoic acid (IV)

The above-mentioned diethyl ether solution containing III was diluted with 200 mL of dichloromethane, 2.7 mL (19.6 mmol) of triethylamine, and 0.5 g of DMAP were added separately, 1.4 mL (19.6 mmol) of acetyl chloride was added dropwise at −10° C. After the dropping, the mixture was stirred at 10° C. for 5 h, then 10 mL of water was added, and stirred at room temperature for 0.5 h. The organic layer was separated, dried over $Na_2SO_4$, filtered and concentrated to give a wax solid. The wax solid was recrystallized from n-hexane to give 1.06 g of white needle crystal, with a yield of 65%. mp 65-66° C. MS (ESI): m/z 249.1 [M−H]−. $^1$H NMR (300 MHz, $CDCl_3$): δ 0.93 (t, 3H, $CH_3$, J=8.5 Hz), 1.37-1.42 (m, 4H, 2×$CH_2$), 1.88-1.91 (m, 2H, $CH_2$), 2.13-2.33 (m, 3H, $COCH_3$), 6.61-6.72 (m, 1H, $OCHCH_2$), 7.37-7.40 (m, 1H, ArH), 7.56-7.62 (m, 2H, ArH), 8.05 (d, 1H, ArH, J=8.1 Hz), 10.98 (brs, 1H, COOH). $^{13}$C NMR (75 MHz, $CDCl_3$): δ 172.0, 166.5, 140.8, 133.1, 130.3, 130.0, 127.1, 125.7, 74.8, 41.0, 36.3, 27.8, 22.4, 13.8.

Example 3

Synthesis of a representative intermediate $V_1$ obtained by coupling 2-(1-acetyl-n-pentyl)benzoic acid with diol 2-(1-acetyl-n-pentyl)benzoic acid (2.50 g, 10.0 mmol) was dissolved in anhydrous dichloromethane (50 mL), EDAC (2.29 g, 12.0 mmol) and a catalytic amount of DMAP were added, stirred at room temperature for 0.5 h, then ethylene glycol (0.62 g, 10.0 mmol) was added, and stirred at room temperature for 5 h. The mixture was filtered, concentrated under reduced pressure, and purified by column chromatography [petroleum ether: ethyl acetate (v:v)=30:1] to give 1.71 g of oily substance, with a yield of 58%. MS (ESI): m/z 317.1 [M+Na]$^+$. $^1$H NMR (300 MHz, $CDCl_3$): δ 0.807 (t, 3H, $CH_3$, J=7.0 Hz), 1.181-1.356 (m, 4H, 2×$CH_2$), 1.730-1.777 (m, 2H, $CH_2$), 1.965 (s, 3H, $COCH_3$), 3.823-3.862 (m, 2H, $CH_2$), 4.269-4.474 (m, 2H, $CH_2$), 5.206 (s, 1H, OH), 6.452 (t, 1H, COOCH, J=6.7 Hz), 7.197-7.265 (m, 1H, ArH), 7.441-7.444 (m, 2H, ArH), 7.750-7.777 (m, 1H, ArH). $^{13}$C NMR (75 MHz, $CDCl_3$): δ 170.90, 167.51, 142.37, 132.15, 129.94, 129.34, 127.39, 126.46, 72.79, 67.05, 60.88, 36.32, 27.90, 22.42, 21.18, 13.92.

Example 4

Synthesis of a Representative Intermediate $V_3$ Obtained by Coupling 2-(1-acetyl-n-pentyl)benzoic Acid with Diamine 2-(1-acetyl-n-pentyl)benzoic acid (2.50 g, 10.0 mmol) was dissolved in anhydrous dichloromethane (50 mL), EDAC (2.29 g, 12.0 mmol) and a catalytic amount of DMAP were added, stirred at room temperature for 0.5 h, then octanediamine (1.44 g, 10.0 mmol) was added, and stirred at room temperature for 8 h. The mixture was filtered, concentrated under reduced pressure, and purified by column chromatography [dichloromethane: methanol (v: v)=10:1] to give 1.92 g of oily substance, with a yield of 51%.

Example 5

Synthesis of a representative intermediate $VI_3$ obtained by coupling telmisartan with diamine Telmisartan (2.57 g, 5.0 mmol) was dissolved in anhydrous dichloromethane (200 mL), EDAC (1.15 g, 6.0 mmol) and a catalytic amount of DMAP were added, stirred at room temperature for 0.5 h, then octanediamine (1.44 g, 10.0 mmol) was added, and the reaction solution was stirred at room temperature for 5 h. The mixture was filtered, concentrated under reduced pressure, and purified by column chromatography [dichloromethane: methanol (v: v)=30:1] to give 1.48 g of white solid, with a yield of 46%. mp: 113° C. MS (ESI): m/z641.4 [M+H]$^+$. $^1$H NMR (300 MHz, $CDCl_3$): δ 0.799 (t, 3H, $CH_3$, J=6.8 Hz), 0.943-1.058 (m, 8H, 4×$CH_2$), 1.506 (m, 4H, 2×$CH_2$), 1.728-1.798 (m, 2H, $CH_2$), 2.374 (s, 3H, $CH_3$), 2.731 (t, 2H, $NH_2CH_2$, J=7.2 Hz), 2.839 (t, 2H, $CH_2$, J=7.7 Hz), 3.137 (t, 2H, $NHCH_2$, J=6.1 Hz), 3.728 (s, 3H, $NCH_3$), 5.398 (s, 2H, $NCH_2$), 7.015 (s, 1H, ArH), 7.041 (s, 1H, ArH), 7.204 (m, 4H, ArH), 7.251-7.312 (m, 6H, ArH), 7.405 (m, 1H, NH), 7.468-7.491 (m, 1H, ArH), 7.670-7.698 (m, 1H, ArH). $^{13}$C NMR (75 MHz, $CDCl_3$): 169.59, 159.58, 154.56, 143.08, 142.47, 140.04, 138.58, 136.45, 136.05, 135.33, 135.08, 130.12, 129.99, 129.44, 129.31, 128.42, 127.69, 126.40, 123.69, 122.71, 122.52, 119.29, 109.63, 109.02, 56.14, 43.98, 39.66, 35.15, 31.90, 31.81, 29.70, 29.33, 26.41, 26.36, 22.66, 16.94, 14.08.

Example 6

Synthesis of 2-O-{2-[(1-acetoxyl)n-pentyl] benzoyl}ethylene glycol telmisartan ester (Is)

The above-mentioned intermediate $V_1$ (1.47 g, 5.0 mmol) was dissolved in anhydrous dichloromethane (30 mL), EDAC (1.15 g, 6.0 mmol) and a catalytic amount of DMAP were added, stirred at room temperature for 0.5 h, then telmisartan (2.57 g, 5.0 mmol) was added, and stirred at room temperature for 8 h. The mixture was filtered, concentrated under reduced pressure, and purified by column chromatography [dichloromethane: methanol (v: v)=50:1] to give 1.69 g of white solid, with a yield of 43%. mp: 82-831. MS (ESI): m/z 791.4 [M+H]+, 813.4 [M+Na]+. $^1$H NMR (300 MHz, $CDCl_3$): δ 0.772 (m, 3H, $CH_3$), 0.989 (m, 3H, $CH_3$), 1.181 (m, 4H, 2×$CH_2$), 1.712 (m, 2H, $CH_2$), 1.808 (m, 2H, $CH_2$), 1.973 (s, 3H, $ArCH_3$), 2.691 (s, 3H, $COCH_3$), 2.871 (m, 2H, $NCNCH_2$), 3.716 (s, 3H, $NCH_3$), 3.973-4.310 (m, 4H, 2×$OCH_2$), 5.369 (s, 2H, $NCH_2$), 6.478 (m, 1H, OCH), 6.948 (s, 1H, ArH), 7.023 (s, 1H, ArH), 7.120-7.302 (m, 7H, ArH), 7.323-7.423 (m, 5H, ArH), 7.722-7.796 (m, 3H, ArH). $^{13}$C NMR (75 MHz, $CDCl_3$): δ 169.19, 167.27, 165.83, 156.09, 154.24, 143.63, 142.67, 142.37, 141.70, 140.76, 136.14, 134.49, 132.12, 131.09, 130.26, 130.01, 129.73, 129.58, 128.97, 128.49, 126.94, 126.65, 125.60, 125.32, 123.44, 121.97, 121.80, 119.02, 109.04, 108.53, 72.35, 62.25, 61.78, 46.50, 36.10, 31.29, 29.29, 27.57, 21.98, 21.45, 20.68, 16.41, 13.59, 13.50.

Example 7

Synthesis of 4-O-{2-[(1-acetoxyl)n-pentyl] benzoyl}butanediol telmisartan ester (z1)

Referring to the method in Example 6, the mono-substituted intermediate (1.61 g, 5.0 mmol) obtained by reacting 2-(1-acetyl-n-pentyl)benzoic acid with butanediol was reacted with telmisartan (2.57 g, 5.0 mmol), and the reaction product was purified by column chromatography to give 1.84 g of white solid, with a yield of 45%. mp: 83° C. MS (ESI): m/z 819.5 [M+H]+, 841.4 [M+Na]+. $^1$H NMR (300 MHz, $CDCl_3$): δ 0.779 (t, 2H, $CH_3$, J=6.9 Hz), 0.855 (t, 1H, $CH_3$, J=7.1 Hz), 0.963 (t, 3H, $CH_3$, J=7.3 Hz), 1.160-1.304 (m, 4H, 2×$CH_2$), 1.495 (m, 2H, $CH_2$), 1.725-1.826 (m, 4H, 2×CH$_2$), 1.952 (s, 3H, ArCH$_3$), 2.676 (s, 3H, COCH$_3$), 2.847 (t, 2H, NCNCH$_2$, J=7.8 Hz), 3.671 (s, 3H, NCH$_3$), 3.926-4.078 (m, 4H, 2×OCH$_2$), 5.339 (s, 2H, NCH$_2$), 6.438 (q, 1H, OCH, J=4.9 Hz), 7.011 (m, 2H, ArH), 7.149-7.413 (m, 14H, ArH), 7.695-7.741 (m, 3H, ArH). $^{13}$C NMR (75 MHz, CDCl$_3$): δ 156.49, 143.71, 141.73, 141.29, 136.64, 134.99, 134.87, 132.30, 131.36, 131.25, 130.76, 130.63, 130.13, 129.93, 129.85, 129.46, 129.07, 127.41, 127.11, 126.15, 126.02, 125.83, 123.90, 122.51, 122.33, 119.49, 109.55, 108.98, 72.86, 64.44, 64.38, 47.04, 36.60, 31.80, 29.81, 28.08, 25.19, 25.08, 22.49, 21.87, 21.18, 16.91, 14.10, 14.01.

Example 8

Synthesis of 8-N-{2-[(1-acetoxyl)n-pentyl]benzoyl}octanediamine telmisartan amide (I$_3$)

Intermediate V$_3$ (1.88 g, 5.0 mmol) was reacted with telmisartan (2.57 g, 5.0 mmol), and the reaction product was purified by column chromatography to give 1.78 g of white solid, with a yield of 41%. mp: 94-95° C. MS (ESI): m/z 873.6 [M+H]+, 895.6 [M+Na]+. $^1$H NMR (300 MHz, CDCl$_3$): δ 0.723 (t, 3H, CH$_3$, J=7.2 Hz), 0.917 (t, 3H, CH$_3$, J=7.3 Hz), 1.130 (m, 8H, 4×CH$_2$), 1.157 (m, 4H, 2×CH$_2$), 1.212 (m, 2H, CH$_2$), 1.414-1.459 (m, 2H, CH$_2$), 1.670-1.775 (m, 4H, 2×CH$_2$), 1.912 (s, 3H, ArCH$_3$), 2.636 (s, 3H, COCH$_3$), 2.786 (t, 2H, NCNCH$_2$, J=7.8 Hz), 2.956 (q, 2H, NHCH$_2$, J=6.6 Hz), 3.266 (q, 2H, NHCH$_2$, J=6.8 Hz), 3.666 (s, 3H, NCH$_3$), 5.302 (s, 2H, NCH$_2$), 5.710 (q, 1H, OCH, J=5.7 Hz), 6.954 (s, 1H, ArH), 6.981 (s, 1H, ArH), 7.134-7.157 (m, 5H, ArH), 7.210-7.263 (m, 9H, ArH), 7.289 (m, 1H, NH), 7.340 (m, 1H, NH), 7.433-7.458 (m, 1H, ArH), 7.603-7.632 (m, 1H, ArH). $^{13}$C NMR (75 MHz, CDCl$_3$): δ 171.16, 169.02, 168.61, 155.93, 154.05, 142.60, 142.16, 139.55, 138.00, 137.87, 136.06, 135.62, 135.58, 134.72, 134.53, 129.56, 129.49, 128.93, 128.82, 127.97, 127.40, 127.20, 127.16, 125.85, 125.25, 123.33, 122.10, 121.89, 118.88, 109.09, 108.48, 73.78, 46.49, 39.40, 39.26, 36.26, 31.42, 31.33, 30.93, 29.68, 29.29, 29.19, 28.86, 28.59, 28.51, 27.17, 26.39, 26.12, 21.82, 21.33, 20.72, 16.44, 13.60, 13.38.

Example 9

Synthesis of 5-O-{2-[(1-acetoxyl)n-pentyl]benzoyl}pentanediol telmisartan ester (I$_4$)

Referring to the method in Example 6, the mono-substituted intermediate (1.68 g, 5.0 mmol) obtained by reacting 2-(1-acetyl-n-pentyl)benzoic acid with pentanediol was reacted with telmisartan (2.57 g, 5.0 mmol), and the reaction product was purified by column chromatography to give 1.98 g of white solid, with a yield of 48%. mp: 78-79° C. MS (ESI): m/z 833.5 [M+H]+, 855.5 [M+Na]+. $^1$H NMR (300 MHz, CDCl$_3$): δ 0.786 (t, 3H, CH$_3$, J=6.9 Hz), 0.964 (t, 3H, CH$_3$, J=7.4 Hz), 1.223-1.256 (m, 6H, 3×CH$_2$), 1.345-1.393 (m, 2H, CH$_2$), 1.571 (t, 2H, CH$_2$, J=7.4 Hz), 1.707-1.802 (m, 4H, 2×CH$_2$), 1.955 (s, 3H, ArCH), 32.681 (s, 3H, COCH$_3$), 2.849 (t, 2H, NCNCH$_2$, J=7.8 Hz), 3.686 (s, 3H, NCH$_3$), 3.958 (t, 2H, OCH$_2$, J=6.5 Hz), 4.132 (t, 2H, OCH$_2$, J=6.6 Hz), 5.356 (s, 2H, NCH$_2$), 6.448 (q, 1H, OCH, J=4.7 Hz), 6.995 (s, 1H, ArH), 7.022 (s, 1H, ArH), 7.140-7.205 (m, 6H, ArH), 7.240-7.314 (m, 2H, ArH), 7.349-7.416 (m, 5H, ArH), 7.696-7.754 (m, 3H, ArH). $^{13}$C NMR (75 MHz, CDCl$_3$): δ 169.82, 167.74, 166.41, 155.98, 154.16, 143.15, 142.63, 142.31, 141.25, 140.78, 136.13, 134.50, 134.28, 131.74, 130.82, 130.27, 129.65, 129.40, 128.95, 128.57, 126.90, 126.59, 125.64, 125.47, 125.33, 123.37, 123.33, 122.03, 121.85, 119.00, 109.05, 108.49, 72.38, 64.34, 64.21, 46.56, 36.12, 31.32, 29.32, 27.68, 27.58, 27.48, 22.00, 21.93, 21.37, 20.69, 16.42, 13.61, 13.52.

Example 10

Synthesis of 6-O-{2-[(1-acetoxyl)n-pentyl]benzoyl}hexanediol telmisartan ester (I$_5$)

Referring to the method in Example 6, the mono-substituted intermediate (1.75 g, 5.0 mmol) obtained by reacting 2-(1-acetyl-n-pentyl)benzoic acid with hexanediol was reacted with telmisartan (2.57 g, 5.0 mmol), and the reaction product was purified by column chromatography to give 1.82 g of white solid, with a yield of 43%. mp: 82-83° C. MS (ESI): m/z 847.5 [M+H]+, 869.5 [M+Na]+. $^1$H NMR (300 MHz, CDCl$_3$): δ 0.796 (m, 3H, CH$_3$), 0.973 (t, 3H, CH$_3$, J=7.2 Hz), 1.176-1.256 (m, 10H, 5×CH$_2$), 1.600 (m, 2H, CH$_2$), 1.757-1.806 (m, 4H, 2×CH$_2$), 1.966 (s, 3H, ArCH$_3$), 2.687 (s, 3H, COCH$_3$), 2.849 (t, 2H, NCNCH$_2$, J=7.7 Hz), 3.702 (s, 3H, NCH$_3$), 3.939-3.961 (m, 2H, OCH$_2$), 4.169 (m, 2H, OCH$_2$), 5.349 (s, 2H, NCH$_2$), 6.443 (q, 1H, OCH), 7.001-7.026 (m, 2H, ArH), 7.154-7.203 (m, 8H, ArH), 7.302-7.405 (m, 5H, ArH), 7.720-7.775 (m, 3H, ArH). $^{13}$C NMR (75 MHz, CDCl$_3$): δ 169.81, 167.77, 166.47, 155.97, 154.15, 143.08, 142.64, 142.30, 141.25, 140.80, 136.13, 134.52, 134.22, 131.68, 130.79, 130.35, 130.25, 129.66, 129.38, 128.96, 128.58, 126.90, 126.59, 125.61, 125.42, 123.35, 122.04, 121.86, 119.01, 109.04, 108.49, 72.42, 64.55, 64.37, 46.56, 36.14, 31.34, 29.24, 28.03, 27.73, 27.59, 25.12, 25.05, 22.01, 21.37, 20.69, 16.42, 13.61, 13.52.

Example 11

Synthesis of 8-O-{2-[(1-acetoxyl)n-pentyl]benzoyl}octanediol telmisartan ester (I$_6$)

Referring to the method in Example 5, the mono-substituted intermediate (1.89 g, 5.0 mmol) obtained by reacting 2-(1-acetyl-n-pentyl)benzoic acid with octanediol was reacted with telmisartan (2.57 g, 5.0 mmol), and the reaction product was purified by column chromatography to give 1.96 g of white solid, with a yield of 45%. mp: 83-84° C. MS (ESI): m/z 875.6 [M+H]+, 897.5 [M+Na]+. $^1$H NMR (300 MHz, CDCl$_3$): δ 0.806 (t, 3H, CH$_3$, J=6.8 Hz), 0.981 (t, 3H, CH$_3$, J=7.3 Hz), 1.179-1.237 (m, 8H, 4×CH$_2$), 1.452-1.474 (m, 6H, 3×CH$_2$), 1.627-1.695 (m, 2H, CH$_2$), 1.722-1.843 (m, 4H, 2×CH$_2$), 1.980 (s, 3H, ArCH$_3$), 2.692 (s, 3H, COCH$_3$), 2.861 (t, 2H, NCNCH$_2$, J=7.8 Hz), 3.712 (s, 3H, NCH$_3$), 3.931 (t, 2H, OCH$_2$, J=6.4 Hz), 4.204 (t, 2H, OCH$_2$, J=6.6 Hz), 5.364 (s, 2H, NCH$_2$), 6.455 (q, 1H, OCH, J=4.6 Hz), 7.001-7.027 (m, 2H, ArH), 7.158-7.286 (m, 8H, ArH), 7.337-7.418 (m, 5H, ArH), 7.703-7.797 (m, 3H, ArH). $^{13}$C NMR (75 MHz, CDCl$_3$): δ 169.81, 167.79, 166.55, 155.97, 154.15, 143.12, 142.60, 141.24, 140.81, 136.11, 134.51, 134.16, 131.63, 130.77, 130.40, 130.24, 129.69, 129.37, 128.95, 128.59, 126.89, 126.58, 125.59, 125.38, 123.39, 122.04, 121.86, 119.02, 109.02, 108.50, 72.47, 64.75, 64.54, 62.40, 46.59, 36.15, 32.24, 31.33, 29.33, 28.85, 28.63, 28.55, 25.45, 25.17, 22.02, 21.37, 20.70, 16.42, 13.61, 13.52.

Example 12

Synthesis of 6-N-{2-[(1-acetoxyl)n-pentyl]benzoyl}hexanediamine telmisartan amide (I$_7$)

Referring to the method in Example 8, the mono-substituted intermediate (1.74 g, 5.0 mmol) obtained by reacting 2-(1-acetyl-n-pentyl)benzoic acid with hexanediamine was reacted with telmisartan (2.57 g, 5.0 mmol), and the reaction product was purified by column chromatography to give 1.69 g of white solid, with a yield of 40%. mp: 96-98° C. MS (ESI): m/z 845.6 [M+H]+, 867.5 [M+Na]+. $^1$H NMR (300 MHz, CDCl$_3$): δ 0.768 (m, 3H, CH$_3$), 0.970 (t, 3H, CH$_3$, J=7.2 Hz), 1.181 (m, 10H, 5×CH$_2$), 1.417 (m, 2H, CH$_2$), 1.776-1.801 (m, 4H, 2×CH$_2$), 1.936 (s, 3H, ArCH$_3$), 2.645 (s, 3H, COCH$_3$), 2.843 (t, 2H, NCNCH$_2$, J=7.6 Hz), 3.013-3.032 (m, 2H, NHCH$_2$), 3.259-3.279 (m, 2H, NHCH$_2$), 3.751 (s, 3H, NCH$_3$), 5.365 (s, 2H, NCH$_2$), 5.749 (m, 1H, OCH), 7.022-7.046 (m, 2H, ArH), 7.195-7.218 (m, 6H, ArH), 7.299-7.328 (m, 9H, ArH), 7.423 (m, 1H, NH), 7.501-7.524 (m, 1H, NH), 7.4674 (m, 1H, ArH). $^{13}$C NMR (75 MHz, CDCl$_3$): δ 171.17, 169.04, 168.62, 155.97, 154.09, 142.63, 142.17, 139.57, 137.94, 136.08, 135.64, 135.52, 134.78, 134.58, 129.62, 129.51, 128.95, 128.84, 127.98, 127.39, 127.23, 127.12, 125.89, 125.29, 123.29, 122.11, 121.92, 118.92, 109.09, 108.50, 73.75, 46.50, 39.17, 39.04, 36.28, 31.37, 29.19, 28.79, 28.43, 27.17, 25.87, 25.68, 21.83, 21.33, 20.69, 16.44, 13.60, 13.38.

Example 13

Synthesis of 4-N-{2-[(1-acetoxyl)n-pentyl]benzoyl}butanediamine telmisartan amide (I$_8$)

Referring to the method in Example 8, the mono-substituted intermediate (1.60 g, 5.0 mmol) obtained by reacting 2-(1-acetyl-n-pentyl)benzoic acid with butanediamine was reacted with telmisartan (2.57 g, 5.0 mmol), and the reaction product was purified by column chromatography to give 1.88 g of white solid, with a yield of 46%. mp: 97-99'C. MS (ESI): m/z 817.5 [M+H]+, 839.5 [M+Na]+. $^1$H NMR (300 MHz, CDCl$_3$): δ 0.743-0.766 (m, 3H, CH$_3$), 0.974 (t, 3H, CH$_3$, J=7.3 Hz), 1.834-1.260 (m, 12H, 6×CH$_2$), 1.835 (s, 3H, ArCH$_3$), 2.696 (s, 3H, COCH$_3$), 2.856 (t, 2H, NCNCH$_2$, J=7.7 Hz), 3.097 (m, 4H, 2×NHCH$_2$), 3.748 (s, 3H, NCH$_3$), 5.382 (s, 2H, NCH$_2$), 5.903 (m, 1H, OCH), 6.998-7.024 (m, 2H, ArH), 7.191-7.215 (m, 6H, ArH), 7.280 (m, 9H, ArH), 7.474 (m, 2H, 2×NH), 7.638 (m, 1H, ArH). $^{13}$C NMR (75 MHz, CDCl$_3$): δ 170.96, 169.22, 168.62, 156.16, 153.91, 142.70, 139.66, 138.30, 138.08, 135.84, 135.30, 134.74, 129.57, 129.33, 129.03, 128.89, 127.87, 127.25, 127.10, 126.84, 125.78, 125.46, 123.27, 122.29, 121.15, 118.69, 109.14, 108.70, 73.52, 46.47, 38.76, 38.52, 36.16, 31.35, 29.16, 27.14, 26.21, 25.69, 21.78, 21.27, 20.52, 16.38, 13.54, 13.31.

Example 14

Synthesis of p-methylbenzoyl octanediamine telmisartan amide (I$_9$)

p-methylbenzoyl chloride (1.55 g, 10.0 mmol) was dissolved in anhydrous dichloromethane (50 mL), triethylamine (2.88 g, 20.0 mmol) and a catalytic amount of DMAP were added, stirred at room temperature for 0.5 h, then octanediamine (1.44 g, 10.0 mmol) was further added, and stirred at room temperature for 3 h. The mixture was filtered, concentrated under reduced pressure, and purified by column chromatography [dichloromethane: methanol (v: v)=20:1] to give 1.52 g of white solid, i.e., a mono-substituted intermediate, with a yield of 48%. The obtained intermediate (1.52 g, 5.8 mmol) was dissolved in anhydrous dichloromethane (30 mL), EDAC (1.15 g, 6.0 mmol) and a catalytic amount of DMAP were added and stirred at room temperature for 0.5 h, then telmisartan (5.96 g, 11.6 mmol) was further added. The reaction mixture was stirred overnight at room temperature, filtered, concentrated under reduced pressure, and purified by column chromatography [dichloromethane: methanol (v: v)=50:1] to give 2.15 g of white solid, with a yield of 49%. MS (ESI): m/z 759.4 [M+H]+, 781.4 [M+Na]+. $^1$H NMR (300 MHz, CDCl$_3$): δ 0.854 (t, 3H, CH$_3$, J=7.6 Hz), 1.25 (m, 8H, 4×CH$_2$), 1.535 (m, 4H, 2×CH$_2$), 1.856 (m, 2H, CH$_2$), 2.342 (s, 3H, ArCH$_3$), 2.756 (s, 3H, ArCH$_3$), 2.881 (t, 2H, CH$_2$, J=6.7 Hz), 3.088 (q, 2H, NHCH$_2$, J=6.6 Hz), 3.404 (q, 2H, NHCH$_2$, J=6.8 Hz), 3.831 (s, 3H, NCH$_3$), 5.398 (s, 2H, NCH$_2$), 7.116 (m, 4H, ArH), 7.287-7.421 (m, 8H, ArH), 7.493 (s, 1H, ArH), 7.583-7.767 (m, 5H, ArH).

Example 15

Synthesis of 3, 5-dichlorobenzoyl octanediamine telmisartan amide (I$_{10}$)

Referring to the method in Example 14, the mono-substituted intermediate (1.59 g, 5.0 mmol) obtained by reacting 3,5-dichlorobenzoic acid with octanediamine was dissolved in anhydrous dichloromethane (30 mL), EDAC (1.15 g, 6.0 mmol) and a catalytic amount of DMAP were added and stirred at room temperature for 0.5 h, then telmisartan (3.86 g, 7.5 mmol) was further added. The mixture was stirred overnight at room temperature, filtered, concentrated under reduced pressure, and purified by column chromatography [dichloromethane: methanol (v: v)=50:1] to give 1.71 g of white soli, with a yield of 42%. MS (ESI): m/z 813.4 [M+H]*, 835.4 [M+Na]*. $^1$H NMR (300 MHz, CDCl$_3$): δ 0.946 (t, 3H, CH$_3$, J=7.3 Hz), 1.124 (m, 8H, 4×CH$_2$), 1.337 (m, 4H, 2×CH$_2$), 1.488 (m, 2H, CH$_2$), 2.666 (s, 3H, ArCH$_3$), 2.709 (t, 2H, CH$_2$, J=6.7 Hz), 3.023 (q, 4H, 2×NHCH$_2$, J=6.7 Hz), 3.795 (s, 3H, NCH$_3$), 5.301 (s, 2H, NCH$_2$), 7.023 (m, 2H, ArH), 7.195-7.327 (m, 10H, ArH), 7.419 (s, 1H, ArH), 7.507 (s, 1H, ArH), 7.565 (d, 1H, ArH), 7.654 (d, 1H, ArH), 7.806 (s, 1H, ArH).

Example 16

Synthesis of 4-cyanobenzoyl octanediamine telmisartan amide (I$_{11}$)

Referring to the method in Example 14, the mono-substituted intermediate (1.37 g, 5.0 mmol) obtained by reacting 4-cyanobenzoic acid with octanediamine was dissolved in anhydrous dichloromethane (30 mL), EDAC (1.15 g, 6.0 mmol) and a catalytic amount of DMAP were added and stirred at room temperature for 0.5 h, then telmisartan (3.86 g, 7.5 mmol) was further added. The mixture was stirred overnight at room temperature, filtered, concentrated under reduced pressure, and purified by column chromatography [dichloromethane: methanol (v: v)=40:1] to give 1.84 g of white solid, with a yield of 48%. MS (ESI): m/z 770.4 [M+H]+, 792.4 [M+Na]+. $^1$H NMR (300 MHz, CDCl$_3$): δ 0.959 (t, 3H, CH3, J=7.3 Hz), 1.183 (m, 4H, 2×CH$_2$), 1.518 (m, 2H, CH$_2$), 1.759 (m, 8H, 4×CH$_2$), 2.678 (s, 3H, ArCH$_3$), 2.789 (t, 2H, CH$_2$, J=6.8 Hz), 3.03 (q, 2H, NHCH$_2$, J=6.5 Hz), 3.385 (q, 2H, NHCH$_2$, J=6.7 Hz), 3.792 (s, 3H, NCH$_3$), 5.306 (s, 2H, NCH$_2$), 7.035 (m, 2H, ArH), 7.194-7.425 (m, 11H, ArH), 7.509 (d, 1H, ArH, J=3.6 Hz), 7.636 (d, 1H, ArH, J=3.4 Hz), 7.751 (d, 2H, ArH, J=4.1 Hz), 7.891 (s, 1H, ArH).

Example 17

Synthesis of p-Nitrobenzoyl Octanediamine Telmisartan Amide ($I_{12}$)

Referring to the method in Example 14, the mono-substituted intermediate (1.47 g, 5.0 mmol) obtained by reacting p-nitrobenzoic acid with octanediamine was dissolved in anhydrous dichloromethane (30 mL), EDAC (1.15 g, 6.0 mmol) and a catalytic amount of DMAP were added and stirred at room temperature for 0.5 h, then telmisartan (3.86 g, 7.5 mmol) was further added, and the mixture was stirred overnight at room temperature, filtered, concentrated under reduced pressure, and purified by column chromatography [dichloromethane: methanol (v: v)=40:1] to give 2.01 g of pale yellow solid. MS (ESI): m/z 790.4 [M+H]+, 812.4 [M+Na]+. H NMR (300 MHz, CDCl$_3$): δ 0.836 (t, 3H, CH$_3$, J=7.3 Hz), 1.103 (m, 8H, 4×CH$_2$), 1.213 (m, 4H, 2×CH$_2$), 1.533 (m, 2H, CH$_2$), 2.652 (s, 3H, ArCH$_3$), 2.771 (t, 2H, CH$_2$, J=7.7 Hz), 3.033 (q, 2H, NHCH$_2$, J=6.3 Hz), 3.342 (q, 2H, NHCH$_2$, J=6.5 Hz), 3.769 (s, 3H, NCH$_3$), 5.282 (s, 2H, NCH$_2$), 7.032 (m, 2H, ArH), 7.192-7.408 (m, 9H, ArH), 7.511 (d, 1H, ArH, J=3.6 Hz), 7.638 (d, 1H, ArH, J=3.6 Hz), 7.789 (d, 1H, ArH, J=4.3 Hz), 7.922 (d, 1H, ArH, J=4.3 Hz), 8.145 (s, 1H, ArH).

Example 18

Synthesis of m-methoxybenzoyl octanediamine telmisartan amide ($I_{13}$)

Referring to the method in Example 14, the mono-substituted intermediate (1.39 g, 5.0 mmol) obtained by reacting m-methoxybenzoic acid with octanediamine was dissolved in anhydrous dichloromethane (30 mL), EDAC (1.15 g, 6.0 mmol) and a catalytic amount of DMAP were added and stirred at room temperature for 0.5 h, then telmisartan (3.86 g, 7.5 mmol) was further added. The mixture was stirred overnight at room temperature, filtered, concentrated under reduced pressure, and purified by column chromatography [dichloromethane: methanol (v: v)=40:1] to give 1.74 g of pale yellow solid, with a yield of 45%. MS (ESI): m/z775.4 [M+H]+, 797.4 [M+Na]+. 1H NMR (300 MHz, CDCl3): δ0.784 (t, 3H, CH3, J=7.3 Hz), 1.012 (m, 8H, 4×CH2), 1.079 (m, 4H, 2×CH2), 1.469 (m, 2H, CH2), 2.683 (s, 3H, ArCH3), 2.819 (t, 2H, CH2, J=7.7 Hz), 3.033 (q, 2H, NHCH2, J=6.5 Hz), 3.342 (q, 2H, NHCH2, J=6.5 Hz), 3.711 (s, 3H, OCH3), 3.767 (s, 3H, NCH3), 5.336 (s, 2H, NCH2), 6.733 (s, 1H, ArH), 6.893 (d, 1H, ArH, J=4.0 Hz), 7.035 (d, 2H, ArH, J=3.8 Hz), 7.212 (M, 6H, ArH), 7.301 (M, 5H, ArH), 7.436 (S, 1H, ArH), 7.529 (d, 1H, ArH, J=3.9 Hz), 7.689 (d, 1H, ArH, J=3.2 Hz).

Example 19

Synthesis of o-Hydroxybenzoyl Octanediamine Telmisartan Amide ($I_{14}$)

Referring to the method in Example 14, o-hydroxybenzoic acid (1.38 g, 10 mmol) was dissolved in anhydrous dichloromethane (50 mL), EDAC (2.29 g, 12.0 mmol) and a catalytic amount of DMAP were added and stirred at room temperature for 0.5 h, octanediamine (1.44 g, 10.0 mmol) was further added. The mixture was stirred at room temperature for 5 h, filtered, concentrated under reduced pressure, and purified by column chromatography [petroleum ether: ethyl acetate (v: v)=30:1] to give 1.34 g of oily substance, with a yield of 44%. The intermediate (1.06 g, 4.0 mmol) was then reacted with telmisartan (2.06 g, 4.0 mmol), and the reaction product was purified by column chromatography to give 1.34 g of white solid, with a yield of 44%. MS (ESI): m/z 783.5 [M+Na]+, 759.4 [M−H]−. $^1$H NMR (300 MHz, CDCl$_3$): δ 0.919-0.967 (m, 7H, CH3, 2×CH$_2$), 0.967-1.096 (m, 4H, 2×CH$_2$), 1.111-1.243 (m, 6H, 3×CH$_2$), 1.422-1.444 (m, 2H, CH$_2$), 1.742-1.766 (m, 2H, CH$_2$), 2.662 (s, 3H, ArCH$_3$), 2.786 (t, 2H, CH$_2$, J=7.5 Hz), 2.996-3.015 (m, 2H, NHCH$_2$), 3.309-3.330 (m, 2H, NHCH$_2$), 3.771 (s, 3H, NCH$_3$), 5.278 (s, 2H, NCH$_2$), 6.554 (t, 1H, ArH, J=7.5 Hz), 6.777-6.804 (m, 1H, ArH), 6.998-7.021 (m, 2H, ArH), 7.122-7.353 (m, 11H, ArH), 7.417 (s, 1H, NH), 7.486-7.549 (m, 2H, ArH), 7.647-7.672 (m, 1H, ArH), 7.863 (m, 1H, NH), 12.664 (s, 1H, OH).

Example 20

Synthesis of 8-N-{2-[(1-acetoxyl)n-pentyl] benzoyl}octanediamine candesartan amide ($I_{15}$)

Referring to the method in Example 8, intermediate $V_3$ (1.88 g, 5.0 mmol) was reacted with candesartan (2.20 g, 5.0 mmol), and the reaction product was purified by column chromatography to give 2.20 g of white solid, with a yield of 55%. MS (ESI): m/z 821.5 [M+Na]+, 797.4 [M−H]−. $^1$H NMR (300 MHz, CDCl$_3$): δ 0.752 (t, 3H, CH$_3$, J=6.9 Hz), 1.153-1.254 (m, 16H, 8×CH$_2$), 1.346 (t, 4H, 2×CH$_2$, J=6.9 Hz), 1.975 (s, 3H, OCH$_3$), 2.975-2.995 (m, 2H, NCH$_2$), 3.282-3.300 (m, 2H, NCH$_2$), 4.309 (q, 2H, OCH$_2$, J=6.6 Hz), 5.331 (s, 2H, CH$_2$), 5.754 (t, 1H, OCH, J=6.9 Hz), 6.087 (s, 1H, NH), 6.642-6.668 (m, 2H, ArH), 6.741-6.767 (m, 2H, ArH), 6.833-6.884 (m, 1H, ArH), 6.973-7.018 (m, 2H, ArH), 7.184-7.248 (m, 2H, ArH), 7.314-7.330 (m, 3H, ArH), 7.409-7.483 (m, 2H, ArH, NH), 7.652-7.676 (m, 1H, NH).

Example 21

Synthesis of 8-N-{2-[(1-acetoxyl)n-pentyl] benzoyl}octanediamine valsartan amide ($I_{16}$)

Referring to the method in Example 8, intermediate $V_3$ (1.88 g, 5.0 mmol) was reacted with valsartan (2.66 g, 5.0 mmol), and the reaction product was purified by column chromatography to give 2.06 g of white solid, with a yield of 52%. MS (ESI): m/z 816.5 [M+Na]+, 792.4 [M−H]−. $^1$H NMR (300 MHz, CDCl$_3$): δ 0.755-0.881 (m, 12H, 4×CH$_3$), 1.183-1.302 (m, 22H, 11×CH$_2$), 1.613-1.635 (m, 2H, CH$_2$), 1.984 (s, 3H, OCH$_3$), 2.399-2.449 (m, 2H, NCH$_2$), 2.953-2.996 (m, 2H, NCH$_2$), 3.307 (s, 2H, NCH), 5.734 (t, 1H, OCH, J=6.6 Hz), 7.194-7.239 (m, 4H, ArH), 7.284-7.354 (m, 5H, ArH), 7.448-7.537 (m, 4H, ArH, NH), 7.999-8.025 (m, 1H, NH).

Example 22

Synthesis of 8-N-{2-[(1-acetoxyl)n-pentyl] benzoyl}octanediamine losartan amide ($I_{17}$)

Referring to the method in Example 8, intermediate $V_3$ (1.60 g, 5.0 mmol) was reacted with losartan (2.08 g, 5.0 mmol), and the reaction product was purified by column chromatography to give 1.88 g of white solid, with a yield of 49%. mp: 197-199° C. MS (ESI): m/z 775 [M+H]+.

Example 23

Synthesis of 8-N-{2-[(1-acetoxyl)n-pentyl] benzoyl}octanediamine telmisartan amide hydrochloride (II)

compound I₃ (873 mg, 1.0 mmol) was dissolved in ethyl acetate, an appropriate amount of saturated solution of HCl in ethyl acetate was added dropwise, and stirred, and solid was precipitated. The solvent was evaporated to give 870 mg of white solid, with a yield of 96%. mp: 227-229° C. MS (ESI): m/z 907.4 [M−H]−.

The above description is only preferred embodiments of the present disclosure, and it should be noted that, several modifications and refinements can be made without departing from the technical principles of the present disclosure for those skilled in the art, which should also be considered as falling within the scope of the present disclosure.

The invention claimed is:

1. A compound which is an optically active butylphthalide-telmisartan hybrid as shown in general formula I, or an optical isomer, an enantiomer, a diastereomer, a racemate or a racemic mixture thereof, or a pharmaceutically acceptable salt thereof:

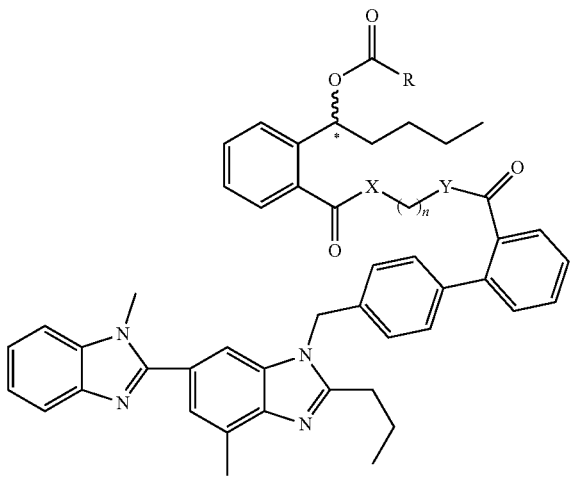

Formula I wherein, R represents a hydrogen atom H, linear or branched C1-C10 alkyl, or (linear or branched C1-C10 alkylene)-Q, wherein Q represents hydroxyl or halogen;

n represents 1 to 20;

X represents an oxygen atom, a nitrogen atom or a sulfur atom;

Y represents an oxygen atom, a nitrogen atom or a sulfur atom; and chiral center * is S or R configurated.

2. The compound or the optical isomer, the enantiomer, the diastereomer, the racemate or the racemic mixture thereof, or the pharmaceutically acceptable salt thereof according to claim 1, wherein R represents a hydrogen atom H;

X represents an oxygen atom or a nitrogen atom; and
Y represents an oxygen atom or a nitrogen atom.

3. The compound or the optical isomer, the enantiomer, the diastereomer, the racemate or the racemic mixture thereof, or the pharmaceutically acceptable salt thereof according to claim 1, wherein the compound is selected from the group consisting of:

2-O-{2-[(1-acetoxyl)-n-pentyl]benzoic acid}hexanediol telmisartan ester;

4-O-{2-[(1-acetoxyl)n-pentyl]benzoyl}butanediol telmisartan ester;

8-N-{2-[(1-acetoxyl)n-pentyl]benzoyl}octanediamine telmisartan amide;

5-O-{2-[(1-acetoxyl)n-pentyl]benzoyl}pentanediol telmisartan ester;

6-O-{2-[(1-acetoxyl)n-pentyl]benzoyl}hexanediol telmisartan ester;

8-O-{2-[(1-acetoxyl)n-pentyl]benzoyl}octanediol telmisartan ester;

6-N-{2-[(1-acetoxyl)n-pentyl]benzoyl}hexanediamine telmisartan amide;

4-N-{2-[(1-acetoxyl)n-pentyl]benzoyl}butanediamine telmisartan amide;

8-N-{2-[(1-acetoxyl)n-pentyl]benzoyl}octanediamine telmisartan amide; and

8-N-{2-[(1-acetoxy)n-pentyl]benzoyl}octanediamine telmisartan amide hydrochloride.

4. A compound or an optical isomer, an enantiomer, a diastereomer, a racemate or a racemic mixture thereof, or a pharmaceutically acceptable salt thereof, wherein the compound is selected from the group consisting of:

p-methylbenzoyl octanediamine telmisartan amide;

3,5-dichlorobenzoyl octanediamine telmisartan amide;

4-cyanobenzoyl octanediamine telmisartan amide;

p-nitrobenzoyl octanediamine telmisartan amide;

m-methoxybenzoyl octanediamine telmisartan amide;

o-hydroxybenzoyl octanediamine telmisartan amide;

8-N-{2-[(1-acetoxyl)n-pentyl]benzoyl}octanediamine candesartan amide;

8-N-{2-[(1-acetoxyl)n-pentyl]benzoyl}octanediamine valsartan amide; and

8-N-{2-[(1-acetoxyl)n-pentyl]benzoyl}octanediamine losartan amide.

5. A preparation method of the compound of general formula I according to claim 1, comprising:

allowing (S)- or (R)-butylphthalide to be saponified and acidified to give a ring-opening lactone compound III, allowing the compound III to be esterified with an acyl chloride compound (RCOCl) to give an ester compound IV, allowing the compound IV to be condensed with a diol or a diamine having a different carbon chain length to give an intermediate V, and allowing the intermediate V to be further condensed with telmisartan to give a target compound I; alternatively, allowing telmisartan to be first condensed with a diol or a diamine having a different carbon chain length to give an intermediate VI, and then allowing the intermediate VI to be condensed with the ester compound IV to give the target compound I; a synthetic route is as follows:

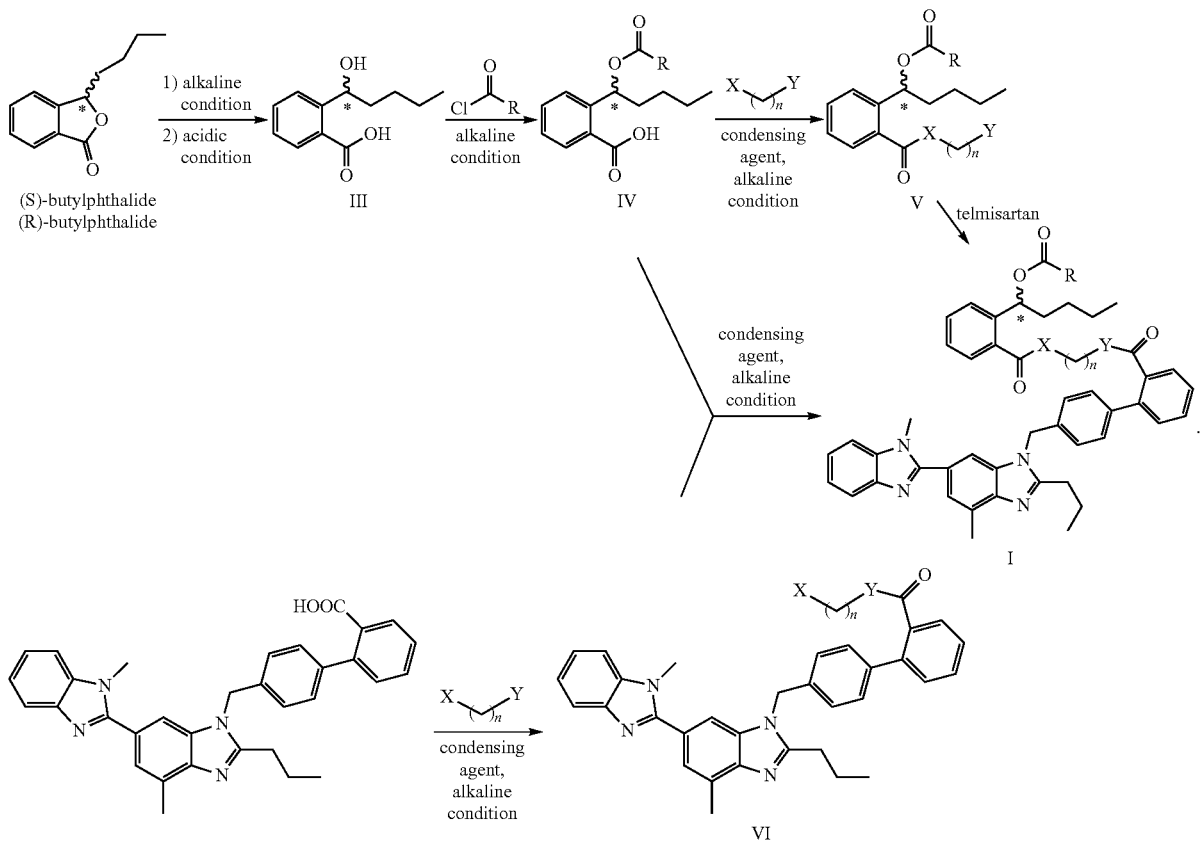

6. The preparation method of the compound of general formula I according to claim 5, wherein,
- the compound IV is prepared from the compound III, by using a solvents selected from one or more of the group consisting of acetonitrile, dichloromethane, chloroform, ethyl acetate, acetone, tetrahydrofuran, N, N-dimethylformamide, dimethyl sulfoxide and dioxane, and a base selected from the group consisting of potassium carbonate, sodium carbonate, sodium bicarbonate, sodium hydroxide, potassium hydroxide, pyridine, 4-methylaminopyridine, triethylamine, and N, N-diisopropylmethylamine, at a reaction temperature from −20° C. to reflux temperature; and/or,
- the compound V is prepared from the compound IV, by using a solvent selected from one or more of the group consisting of acetonitrile, dichloromethane, chloroform, ethyl acetate, acetone, tetrahydrofuran, N, N-dimethylformamide, dimethyl sulfoxide and dioxane, a condensing agent selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide, and a base selected from the group consisting of pyridine, 4-methylaminopyridine, triethylamine, and N, N-diisopropylmethylamine, at a reaction temperature from −20° C. to reflux temperature; and/or,
- the compound I is prepared from the compound V, by using a solvent selected from one or more of the group consisting of acetonitrile, dichloromethane, chloroform, ethyl acetate, acetone, tetrahydrofuran, N, N-dimethylformamide, dimethyl sulfoxide and dioxane, a condensing agent selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide, and a base selected from the group consisting of pyridine, 4-methylaminopyridine, triethylamine, and N, N-diisopropylmethylamine, at a reaction temperature from −20° C. to reflux temperature; and/or,
- the compound VI is prepared from telmisartan, by using a solvent selected from one or more of the group consisting of acetonitrile, dichloromethane, chloroform, ethyl acetate, acetone, tetrahydrofuran, N, N-dimethylformamide, dimethyl sulfoxide and dioxane, a condensing agent selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide; and a base selected from the group consisting of pyridine, 4-methylaminopyridine, triethylamine, and N, N-diisopropylmethylamine, at a reaction temperature from −20° C. to reflux temperature; and/or,
- the compound I is prepared from the compound IV and the compound VI, by using a solvent selected from one or more of the group consisting of acetonitrile, dichloromethane, chloroform, ethyl acetate, acetone, tetrahydrofuran, N, N-dimethylformamide, dimethyl sulfoxide and dioxane, a condensing agent selected from the group consisting of N, N'-dicyclohexylcarbodiimide, 1-(3-dimethylaminopropyl)-3-ethylcarbodiimide hydrochloride, 1-hydroxybenzotriazole, and N-hydroxysuccinimide, and a base selected from the group consisting of pyridine, 4-methylaminopyridine, triethylamine, and N, N-diisopropylmethylamine, at a reaction temperature from −20° C. to reflux temperature.

7. The preparation method of the compound of general formula I according to claim 6, wherein, the compound IV is prepared from the compound III, by using dichloromethane as the solvent and triethylamine as the base, at the reaction temperature of −20° C.; and/or, the compound V is prepared from the compound IV, by using dichloromethane as the solvent, 1-(3-dimethylaminopropyl)-3-ethylcarbodiimide hydrochloride as the condensing agent, and 4-methylaminopyridine as the base, at the reaction temperature of room temperature; and/or, the compound I is prepared from the compound V, by using dichloromethane as the solvent, 1-(3-dimethylaminopropyl)-3-ethylcarbodiimide hydrochloride as the condensing agent, and 4-methylaminopyridine as the base, at the reaction temperature of room temperature; and/or, the compound VI is prepared from telmisartan, by using dichloromethane as the solvent, 1-(3-dimethylaminopropyl)-3-ethylcarbodiimide hydrochloride as the condensing agent, and 4-methylaminopyridine as the base, at the reaction temperature of room temperature; and/or, the compound I is prepared from the compound IV and compound VI, by using dichloromethane as the solvent, 1-(3-dimethylaminopropyl)-3-ethylcarbodiimide hydrochloride as the condensing agent, and 4-methylaminopyridine as the base, at the reaction temperature of room temperature.

8. A pharmaceutical composition comprising a therapeutically effective amount of the compound of general formula I, or the optical isomer, the enantiomer, the diastereomer, the racemate or the racemic mixture thereof, or the pharmaceutically acceptable salt thereof according to claim 1, and a medicinal carrier, adjuvant or vehicle.

9. A method of treating cerebral ischemic stroke, comprising:

administrating to a mammal a pharmaceutical composition comprising the compound, or the optical isomer, the enantiomer, the diastereomer, the racemate or the racemic mixture thereof, or the pharmaceutically acceptable salt thereof according to claim 1.

* * * * *